United States Patent [19]

Shutske et al.

[11] Patent Number: 4,873,234

[45] Date of Patent: Oct. 10, 1989

[54] ISOXAZOLOBENZOXAZEPINES

[75] Inventors: Gregory M. Shutske, Somerset; Kevin J. Kapples, Little York, both of N.J.

[73] Assignee: Hoechst-Roussel Pharmaceuticals Inc., Somerville, N.J.

[21] Appl. No.: 226,930

[22] Filed: Aug. 1, 1988

[51] Int. Cl.[4] ................... C07D 448/04; A61K 31/55
[52] U.S. Cl. ................................. 514/211; 540/488; 540/548
[58] Field of Search ................ 540/548, 488; 514/211

[56] References Cited

U.S. PATENT DOCUMENTS 4,476,133 10/1984 Hirai ................................. 540/548

Primary Examiner—Robert Gerstl
Attorney, Agent, or Firm—Jerome Rosenstock

[57] ABSTRACT

This invention relates to isoxazolobenzoxazepines having the following formula

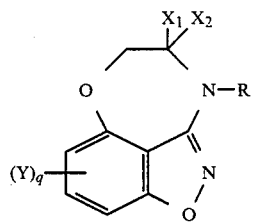

wherein $X_1$ is H; $X_2$ is H or OH; or $X_1$ and $X_2$ taken together are carbonyl oxygen or

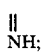

R is (1) H, (2) loweralkyl, (3) arylloweralkyl, (4) loweralkynyl, (5) loweralkenyl,

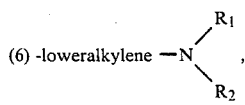

where $R_1$ and $R_2$ are independently (a) H, (b) lower alkyl, (c) arylloweralkyl, (d) lower alkylene

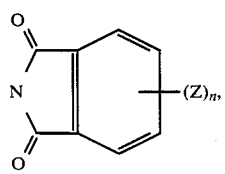

where Z is H, halogen, loweralkyl, loweralkoxy, $CF_3$, nitro or amino and n is a integer of 1 to 3;

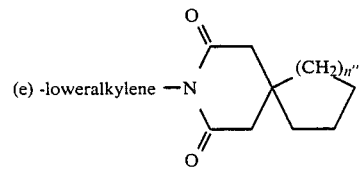

where n″ is an integer of 1 to 3; or (f) $R_1$ and $R_2$ taken together with the nitrogen atom are substituted or unsubstituted piperidino or pyrrolidino of the formula

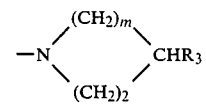

where $R_3$ is H, loweralkyl or aryl, and m is an integer of 1 to 2;

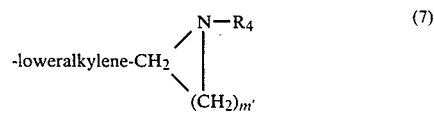

(7)

wherein $R_4$ is H or loweralkyl and m′ is an integer of 3 to 4;

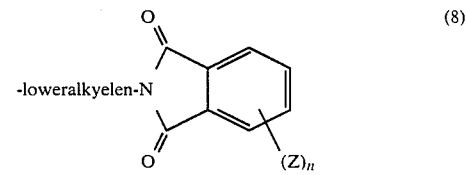

(8)

where Z and n are as previously defined;

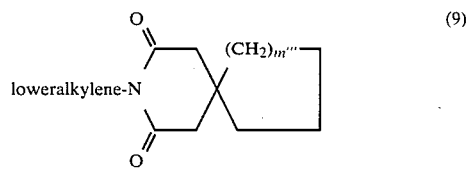

(9)

where m‴ is an integer of 1,2 or 3

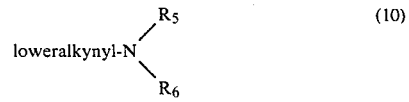

(10)

where $R_5$ and $R_6$ are lower alkyl, aryl lower alkyl or are independently taken together with the N atom to form a substituted or unsubstituted piperidino or pyrrolidino group of the formula (Abstract continued on next page.)

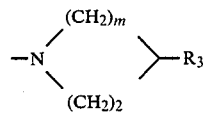
where $R_3$ and m are as previously defined
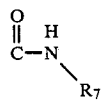 (11)
where $R_7$ is loweralkyl, aryl, or arylloweralkyl;
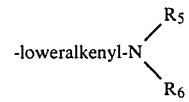 (12)
where $R_5$ and $R_6$ are as previously defined; and the pharmaceutically acceptable acid addition salts thereof and where applicable to the geometric, stereo and optical isomers thereof.
108 Claims, No Drawings

ISOXAZOLOBENZOXAZEPINES

This invention relates to isoxazolobenzoxazepines having the following formula

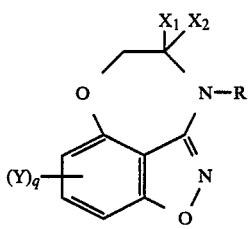
(I)

wherein $X_1$ is H; $X_2$ is H or OH; or $X_1$ and $X_2$ taken together are carbonyl oxygen or

NH;

R is (1) H, (2) loweralkyl, (3) arylloweralkyl, (4) loweralkynyl, (5) loweralkenyl,

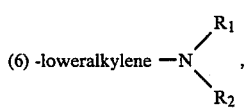

where $R_1$ and $R_2$ are independently (a) H, (b) lower alkyl, (c) arylloweralkyl (d) lower alkylene

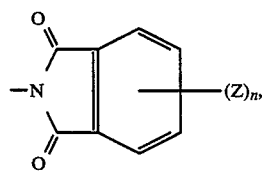

where Z is H, halogen, loweralkyl, loweralkoxy, $CF_3$, nitro or amino and n is a integer of 1 to 3;

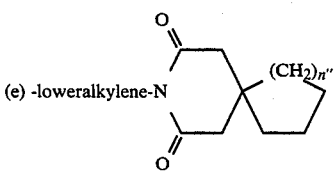

where n'' is an integer of 1 to 3; or (f) $R_1$ and $R_2$ taken together with the nitrogen atom are substituted or unsubstituted piperidino or pyrrolidino of the formula

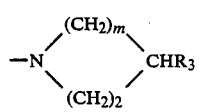

where $R_3$ is H, loweralkyl, or aryl, and m is an integer of 1 or 2;

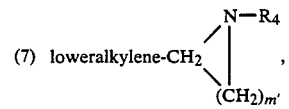

where $R_4$ is H or loweralkyl and where m' is an integer of 3 or 4;

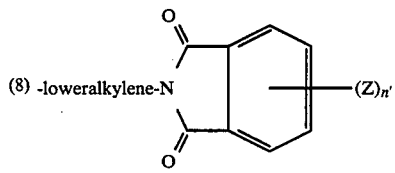

where Z and n are as previously defined;

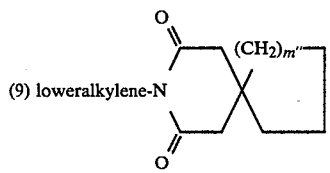

where m''' is an integer of 1,2 or 3;

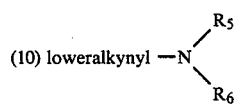

where $R_5$ and $R_6$ are independently lower alkyl, aryl lower alkyl or are taken together with N atom to form a substituted or unsubstituted piperidino or pyrrolidino group of the formula

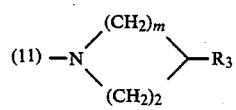

where $R_3$ and m are as previously defined;

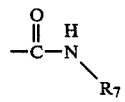

where $R_7$ is lower alkyl, aryl or aryl lower alkyl;

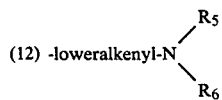

where $R_5$ and $R_6$ are as previously defined;

Throughout the specification and appended claims, a given chemical formula or name shall encompass all geometric, optical and stereoisomers thereof where such isomers exist.

In the above definition, the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; the term "arylloweralkyl" refers to a monovalent substituent which consists of a single aryl group, e.g. phenyl, o-toluyl, m-methoxyphenyl, etc., of the formula

where Z and n are as defined below, or a plurality of aryl groups linked through a loweralkylene group having its free valence bond from a carbon of the loweralkylene group, and having a formula of

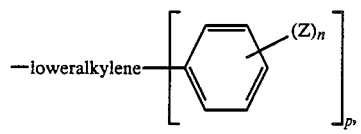

where p is an integer of 1 or 2; where Z is hydrogen, halogen, loweralkyl, loweralkoxy, $CF_3$, $NO_2$ or $NH_2$ and n is an integer of 1 to 3; the term "alkylene" refers to a bivalent radical of the lower branched or unbranched alkyl group it is derived from having valence bonds from two terminal carbons thereof, e.g. ethylene ($-CH_2-CH_2-$), propylene ($-CH_2CH_2CH_2-$), isopropylene

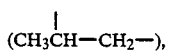

etc; the term "alkynyl" refers to a straight or branched chain hydrocarbon containing one unsatruated carbon to carbon triple bond, e.g. $-C\equiv C-$, $-CH_2-C\equiv C-$, etc; the term "alkenyl" refers to a straight or branched chain hydrocarbon containing one unsaturated carbon to carbon double bond, e.g. $-CH=CH-$, $-CH_2CH=CH-$,

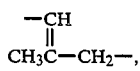

etc; and the term "halogen" refers to a member of the halogen family consisting of fluorine, chlorine, bromine and iodine.

The compounds of the present invention are prepared in the following manner. The substituents, R, $R_1$, $R_2$, $R_3$, $R_4$, $X_1$, $X_2$ and Y and the integer n are as defined above unless indicated otherwise.

A 1,2-benzisoxazole of the formula II is selected,

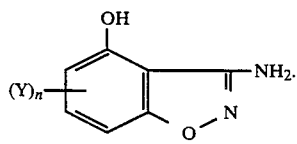

Such benzisoxazoles are well known or can easily be obtained using conventional chemical techniques. For example, a fluorine substituted benzene having the formula

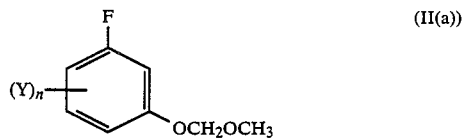

is reacted with an alkyl lithium, e.g. n-butyl lithium, under standard organometallic reagent forming conditions to form an aryl lithium reagent of the formula

which in turn is reacted with N,N,-dimethylformamide under standard conditions, such as for example in a non-polar solvent, e.g. tetrahydrofuran, ether, etc. at a temperature of $-80°$ to $-40°$ C. for 0.5 to 4 hours, to form a benzaldehyde of the formula (II(c))

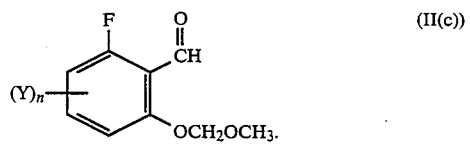

Compound II(c) in turn is reacted with hydroxylamine hydrochloride under standard oxime formation conditions, e.g. in a basic solvent, such as pyridine, picoline, etc., at a temperature of 80° to 150° C. for 0.5 to 5 hours to form the oxime

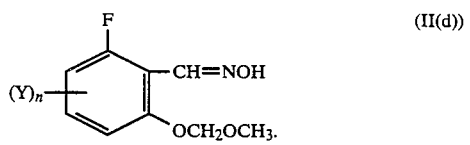

Compound II(d) is reacted with conventional reagents to convert an oxime to a nitrile. For example, Compound II(d), is reacted with trichloroacetyl chloride in an inert solvent, e.g. methylene chloride, benzene, toluene etc., at a temperature of 25° to 120° C. for 0.5 to 5 hours, to form a nitrile having the formula

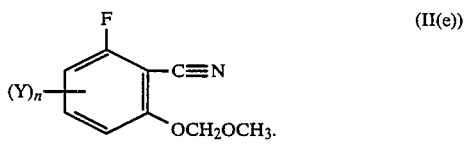

Compound IIe in turn is reacted with the potassium anion of acetone oxime, generated from potassium tertiary butoxide and acetone oxime, in a solvent, e.g. tetrahydrofuran, dimethylformamide, etc., at a temperature of 0° to 50° C. for 0.5 to 5 hours, to form Compound II(f)

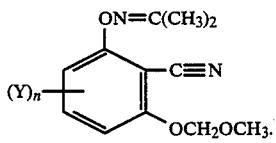 (II(f))

Compound II(f) is then subjected to an acid catalyzed deprotection and ring closure by reaction with a saturated ethereal mineral acid solution, e.g. HCl or HBr solution in a polar, protic solvent, e.g. methanol, ethanol, isopropanol, etc., at a temperature of 25° to 80° C. for 1 to 24 hours to form compound II.

To form Compound I of the invention where R is H and $X_1$ and $X_2$ together form a carbonyl oxygen

Compound II is reacted with a halo-substituted acetic acid ester of the formula Hal

 (III)

where Hal is halogen and $R_8$ is lower alkyl, under conventional nucleophilic reaction conditions, e.g. in a polar, aprotic solvent such as acetone, tetrahydrofuran, dimethylformamide, etc., at a temperature of 25° to 120° C. for 1 to 8 hours, in the presence of a base such as potassium carbonate or trimethylamine, to form Compound IV of the formula

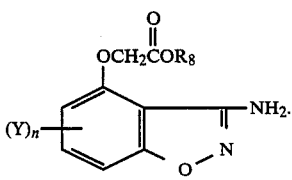 (IV)

Compound IV in turn is subjected to reaction with a condensation agent, e.g. a strong base such as NaH, KH, potassium t-butoxide, etc., under conventional condensation conditions, in a polar aprotic solvent, e.g. tetrahydrofuran, dimethylformamide, etc., at a temperature of 0° to 50° C. for 0.5 to 5 hours, to form Compound V of the invention

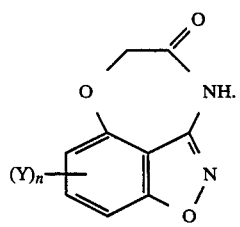 (V)

To obtain Compound I of the invention where $R_1$ is H and $X_1$ and $X_2$ are each hydrogen, Compound II is reacted with a di-halo ethane, Hal—$CH_2$—$CH_2$ Hal, where Hal is a halogen, under conventional nucleophilic reaction conditions. Typically, the reaction is conducted in a polar aprotic solvent, e.g. dimethoxyethane, tetrahydrofuran, dimethylformamide, etc., at a temperature of 25° to 120° C. for 1 to 8 hours in the presence of a base such as $K_2CO_3$ or NaH, to form Compound VI, where Hal is a halogen

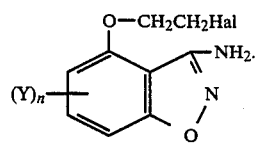 (VI)

Compound VI is subjected to condensation with a condensation agent, as described above, to form Compound VII of the invention

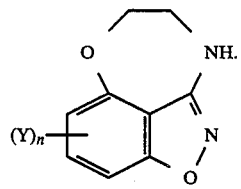 (VII)

Alternatively, Compound VII can be obtained by subjecting Compound V to a reduction of the carbonyl group by reaction with a strong reducing agent, such as a metal hydride, e.g. $BH_3$, or mixtures of lithium aluminum hydroxide and a Lewis acid e.g. $AlCl_3$, using conventional conditions such as a polar aprotic solvent, e.g. tetrahydrofuran, dimethoxy ethane, at a temperature of 25° to 80° C. for 1 to 8 hours.

To obtain Compound I of the invention where $R_1$ is H, $X_1$ and $X_2$ taken together is NH, Compound II is reacted with chloroacetonitrile in the presence of a polar aprotic solvent, e.g. acetone, THF, DMF etc., at a temperature of 25° to 120° C. for 1 to 8 hours to form Compound VIII.

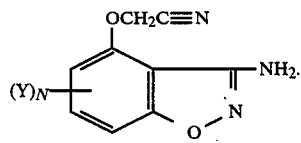 (VIII)

Compound VIII, in turn, is subjected to ring closure by reaction with a condensation agent, e.g. NaH, as previously described, to form Compound IX of the invention

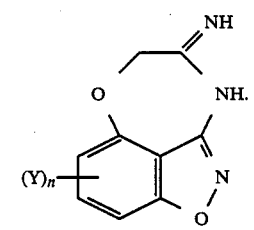 (IX)

To obtain Compound I of the invention where $X_1$ is OH and $X_2$ is H, Compound V is reacted with a metal hydride, e.g. $LiAlH_4$, sodium bis(2-methoxy ethoxy)aluminum hydride, etc., in a polar solvent, e.g. ether, tetrahydrofuran, benzene, etc., at a temperature of 0° to 25° C. for 0.5 to 5 hours to form Compound

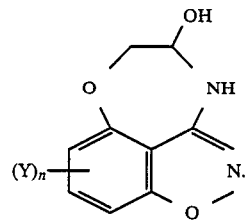

Compounds V, VII, or IX are reacted with Compound XI, Hal-R₄, where Hal is a halogen and R₄ is selected from lower alkyl; arylloweralkyl; loweralkynyl; loweralkenyl;

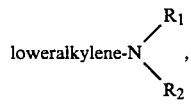

where $R_1$ and $R_2$ are independently H or loweralkyl or $R_1$ and $R_2$ taken together with the nitrogen atom are piperidino or pyrrolidino of the formula

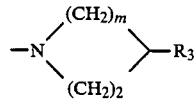

where $R_3$ is H, loweralkyl or aryl of the formula

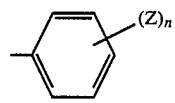

where Z and n are as previously defined, and m is an integer of 3 or 4;

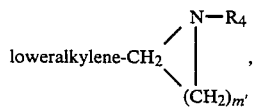

where $R_5$ is H, or lower alkyl and n' is an integer of 3 or 4;

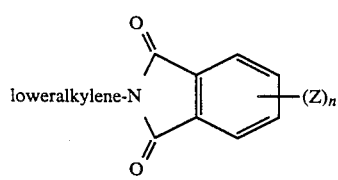

where Z and n are as previously defined;

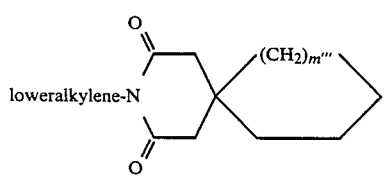

where m''' is an integer of 1 to 3. This reaction is conducted under nucleophilic reaction conditions to form Compound XII of the invention, having the formula

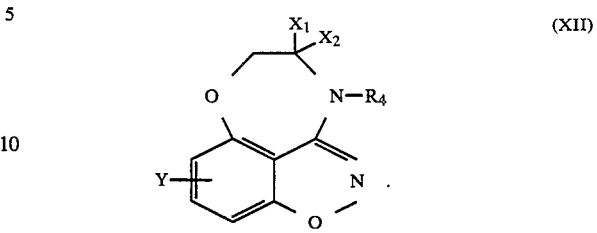

Typically, the reaction is carried out in a polar aprotic solvent e.g. dimethylformamide, tetrahydrofuran, dimethylsulfoxide, etc., at a temperature of 25° to 150° C. for 1 to 8 hours with a strong base such as NaH or potassium-t-butoxide.

In an alternative embodiment, Compounds V, VII or IX are reacted with Compound XIII of the formula Q-R₄, where Q is mesyl

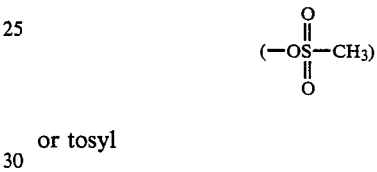

or tosyl

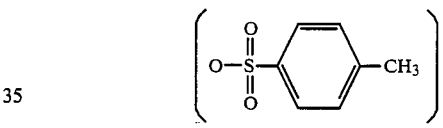

and R₄ is as previously defined, under the reaction conditions described above, to form Compound XII(a),

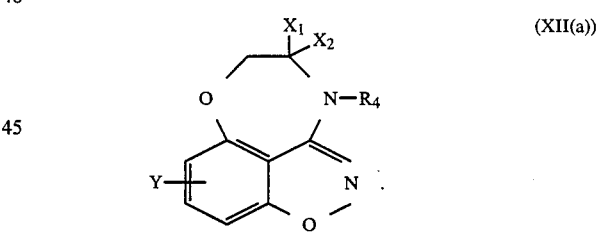

Typically the reaction is conducted in a polar aprotic solvent, e.g. tetrahydrofuran, dimethylformamide, dimethylsulfoxide, etc., at a temperature of 25° to 150° C. for 1 to 8 hours with a strong base such as NaH or potassium t-butoxide.

In a further alternative, Compound VIII is treated successively, under the condensation conditions described above, e.g. a strong base such as NaH or KH, in a solvent such as tetrahydrofuran or dimethylformamide at 0° to 50° for 0.5 to 5 hours followed by treatment with compound XI, Hal-R₄, as described above, followed by an aqueous work-up.

Compound XII where $X_1$ and $X_2$ together form a carbonyl oxygen is treated with a metal hydride reducing agent, e.g. BH₃, or mixtures of LiAlH₄ and a Lewis acid, etc., as previously described above, to form Compound XII where $X_1$ and $X_2$ are each hydrogen. Alternatively, Compound XII where $X_1$ and $X_2$ together form a carbonyl oxygen may be treated with a metal hydride, e.g. LiAlH$_4$, as described above, to form Compound XII where X$_1$ is OH and X$_2$ is hydrogen.

Compound XII where R$_4$ is loweralkylene -N(CH$_3$)$_2$ is converted to Compound XII, where R$_4$ is

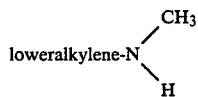

by treatment with a chloroformate such as 1-chloroethylchloroformate or phenyl chloroformate in an inert solvent, such as CH$_2$Cl$_2$ or benzene at a temperature of 0° to 25° C. for 1 to 24 hours, and hydrolysis of the resulting carbamate in an alcoholic solvent such as methanol, isopropanol or isobutanol, at 50°–120° C. for 1 to 24 hours. This compound in turn can be reacted with a higher alkyl halide, e.g. ethyl chloride, under conventional reaction conditions, to form a dialkyl amine substituent, e.g.

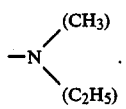

Compound XII where R$_4$ is loweralkynyl is reacted with an amine selected from

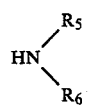 (XIV)

where R$_5$ and R$_6$ are as defined above, in the presence of paraformaldehyde and cuprous chloride to form Compound XV of the invention,

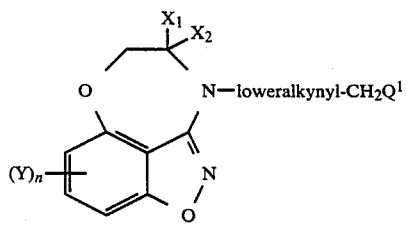

where Q$^1$ is

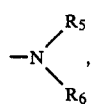

Compound XII where X$_1$ and X$_2$ are both H can be reacted with an alkylisocyanate of the formula R$_7$-N=C=O (XXI), where R$_7$ is loweralkyl, aryl, or aryl loweralkyl in the presence of a strong base such as NaH or potassium t-butoxide to form Compound XXII of the invention in the presence of a strong base such as NaH or potassium t-butoxide

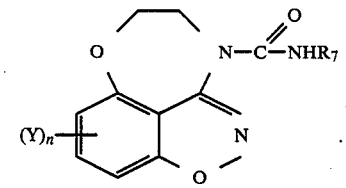 (XVI)

Compound XII where R$_4$ is

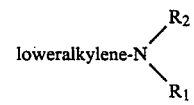

where at least R$_1$ or R$_2$ is hydrogen, is reacted with a tosylate or mesylate of the formula Q''-R$_8$ (XVII), where Q'' is the tosylate or mesylate moiety and R$_8$ is

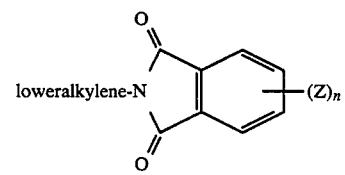

where Z and n are as previously defined above, and

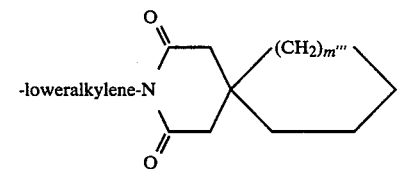

where m''' is as previously defined, to form a compound of the invention having the formula

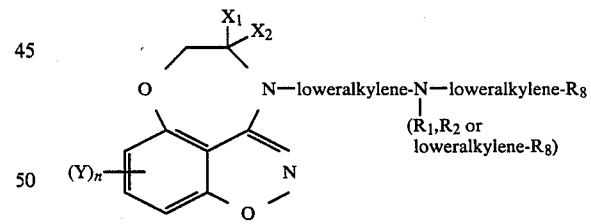

Typically this reaction is carried out under conventional alkylating reaction conditions, in a polar aprotic solvent, e.g., dimethylformamide, tetrahydrofuran, dimethylsulfoxide, etc., at a temperature of 25° to 120° C. for 1 to 24 hours.

Compounds of the instant invention include:
3-Propylisoxazolo[3,4,5-ef][1,4]benzoxazepin-4(5H)-one;
3-Butylisoxazolo[3,4,5,-ef][1,4]benzoxazepin-4(5H)-one;
3-(2-Methylpropyl)isoxazolo[3,4,5-ef][1,4]benzoxazepin-4(5H)-one;
3-(2-Methylethyl)isoxazolo[3,4,5-ef][1,4]benzoxazepin-4(5H)-one;
3-(2-Phenylethyl)isoxazolo[3,4,5-ef][1,4]benzoxazepin-4(5H)-one;

3-(4,4-Diphenylbutyl)isoxazolo[3,4,5-ef][1,4]benzoxazepin-4(5H)-one;
3-(3-Phenylpropyl)isoxazolo[3,4,5-ef][1,4]benzoxazepin-4(5H)-one;
3-(2-Propenyl)isoxazolo[3,4,5-ef][1,4]benzoxazepin-4(5H)-one;
3-(2-Dimethylaminoethyl)isoxazolo[3,4,5-ef][1,4]benzoxazepin-4(5H)-one;
3-(3-Methylaminopropyl)isoxazolo[3,4,5-ef][1,4]benzoxazepin-4(5H)-one;
3-(2-Methylaminoethyl)isoxazolo[3,4,5-ef][1,4]benzoxazepin-4(5H)-one;
3-(2-Diethylaminoethyl)isoxazolo[3,4,5-ef][1,4]benzoxazepin-4(5H)-one;
3-(2-(1-Pyrrolidinyl)ethyl)isoxazolo[3,4,5-ef][1,4]benzoxazepin-4(5H)-one;
3-(2-(1-Piperidinyl)ethyl)isoxazolo[3,4,5-ef][1,4]benzoxazepin-4(5H)-one;
3-(2-(4-Morpholinyl)ethyl)isoxazolo[3,4,5-ef][1,4]benzoxazepin-4(5H)-one;
3-[(1-Methyl-2-pyrrolidinyl)methyl]isoxazolo[3,4,5-ef][1,4]benzoxazepin-4(5 H)-one;
3-[(1-Methyl-2-piperidinyl(methyl]isoxazolo[3,4,5-ef][1,4]benzoxazepin-4(5H)-one;
4,5-Dihydro-3-propylisoxazolo[3,4,5-ef][1,4]benzoxazepine;
3-Butyl-4,5-dihydroisoxazolo[3,4,5-ef][1,4]benzoxazepine;
4,5-Dihydro-3-(2-methylpropyl)isoxazolo[3,4,5-ef][1,4]benzoxazepine;
4,5-Dihydro-3-(1-methylethyl)isoxazolo[3,4,5-ef][1,4]benzoxazepine;
4,5-Dihydro-3-(2-phenylethyl)isoxazolo[3,4,5-ef][1,4]benzoxazepine;
4,5-Dihydro-3-(phenylmethyl)isoxazolo[3,4,5-ef][1,4]benzoxazepine;
4,5-Dihydro-3-(4,4-bis(4-fluorophenyl)butyl)isoxazolo[3,4,5-ef][1,4]benzoxazepine;
4,5-Dihydro-3-(3-phenylpropyl)isoxazolo[3,4,5-ef][1,4]benzoxazepine;
4,5-Dihydro-3-(2-propenyl)isoxazolo[3,4,5-ef][1,4]benzoxazepine;
4,5-Dihydro-3-(2-diethylaminoethyl)isoxazolo[3,4,5-ef][1,4]-benzoxazepine;
4,5-Dihydro-3-(2-(1-pyrrolidinyl)ethyl)isoxazolo[3,4,5-ef][1,4]benzoxazepine;
4,5-Dihydro-3-(2-(1-piperidinyl)ethyl)isoxazolo[3,4,5-ef][1,4]benzoxazepine;
3,4-Dihydro-3-(2-(4-morpholinyl)ethyl)isoxazolo[3,4,5-ef][1,4]benzoxazepine;
3,4-Dihydro-3-[(1-methyl-2-piperidinyl)methyl]isoxazolo[3,4,5-ef][1,4]benzoxazepine;
4,5-Dihydro-3-propylisoxazolo[3,4,5-ef][1,4]benzoxazepin-4-ol;
3-Butyl-4,5-dihydroisoxazolo[3,4,5-ef][1,4]benzoxazepin-4-ol;
4,5-Dihydro-3-(2-methylpropyl)isoxazolo[3,4,5-ef],1,4]benzoxazepin-4-ol;
4,5-Dihydro-3-(1-methylethyl)isoxazolo[3,4,5-ef][1,4]benzoxazepin-4-ol;
4,5-Dihydro-3-(2-phenylethyl)isoxazolo[3,4,5-ef][1,4]benzoxazepin-4-ol;
4,5-Dihydro-3-(phenylmethyl)isoxazolo[3,4,5-ef][1,4]benzoxazepin-4-ol;
4,5-Dihydro-3-(4,4-bis(4-fluorophenyl)butyl)isoxazolo[3,4,5-ef][1,4]benxozazepin-4-ol;
4,5-Dihydro-3-(3-phenylpropyl)isoxazolo[3,4,5-ef][1,4]benzoxazepin-4-ol;
4,5-Dihydro-3-(ethylaminocarbonyl)isoxazolo[3,4,5-ef][1,4]benzoxazepine;
4,5-Dihydro-3-(propylaminocarbonyl)isoxazolo[3,4,5-ef][1,4]benzoxazepine;
4,5-Dihydro-3-(butylaminocarbonyl)isoxazolo[3,4,5-ef][1,4]benzoxazepine;
4,5-Dihydro-3-(phenylaminocarbonyl)isoxazolo[3,4,5-ef][1,4]benzoxazepine;
3-(4-Dimethylamino-2-butynyl)isoxazolo[3,4,5-ef][1,4]benzoxazepin-4(5H)-one;
3-(4-Diethylamino-2-butynyl)isoxazolo[3,4,5-ef][1,4]benzoxazepin-4(5H)-one;
3-(4-(4-Morpholinyl)-2-butynyl)isoxazolo[3,4,5-ef][1,4]benzoxazepin-4(5H)-one;
3,4-Dihydro-3-(4-dimethylamino-2-butynyl)isoxazolo[3,4,5-ef][1,4]benzoxazepine;
3,4-Dihydro-3-(4-diethylamino-2-butynyl)isoxazolo[3,4,5-ef][1,4]benzoxazepine;
3,4-Dihydro-3-(4-(1-pyrrolidinyl)-2-butynyl)isoxazolo[3,4,5-ef][1,4]benzoxazepine;
3,4-Dihydro-3-(4-(1-piperidinyl)-2-butynyl)isoxazolo[3,4,5-ef][1,4]benzoxazepine;
3,4-Dihydro-3-(4-(4-morpholinyl)-2-butynyl)-2-butynyl)isoxazolo[3,4,5-ef][1,4]benzoxazepine Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)]. The analgesic activity of some of the compounds expressed in terms of percent inhibition of writhing are given in TABLE I.

TABLE I

| Compound | Dose (subcutaneous) (mg/kg of body weight) | Inhibition Writhing (%) |
|---|---|---|
| 4,5-dihydroisoxazolo-[3,4,5-ef][1,4]benzoxazepine | 20 | 45 |
| 4,5-dihydro-3-methylisoxazolo-[3,4,5-ef][1,4]benzoxazepin-4-ol | 20 | 66 |
| 4,5-dihydroisoxazolo-[3,4,5-ef][1,4]benzoxazepin-4-ol | 20 | 45 |
| 3-(3-dimethylaminopropyl)isoxazolo-[3,4,5-ef][1,4]benzoxazepin-4(5H)—one, fumarate | 20 | 44 |
| 4,5-dihydro-3-(3-dimethylaminopropyl)-isoxazolo[3,4,5-ef][1,4]benzoxazepine, sesquifumarate | 20 | 42 |
| 3-(2-phthalimidoethyl)isoxazolo[3,4,5-ef]-[1,4]benzoxazepin-4(5H)—one | 20 | 39 |
| (S)—4,5-dihydro-3-[(1-methyl-2-pyrrolidinyl)-methyl]isoxazolo[3,4,5-ef][1,4]benzoxazepine, fumarate, hemihydrate | 20 | 46 |
| 3-(phenylmethy)isoxazolo[3,4,5-ef][1,4]benzoxazepin-4(5H)—one | 20 | 46 |
| 4,5-dihydro-3-(4,4-diphenyl butyl)isoxazolo[3,4,5-ef][1,4]benzoxazepine | 20 | 49 |
| 4,5-dihydro-3-(2-propyl)isoxazolo[3,4,5-ef][1,4]benzoxazepine | 20 | 42 |
| 3-(2-propynyl)isoxazolo-[3,4,5-ef][1,4]benzoxazepin-4(5H)—one | 20 | 48 |
| Acetylsalicylic acid | 53 | 50(ED$_{50}$) |

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing fums and the like. These preparations should contain at least 4% of the isoxazolobenzoxazepine derivatives of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the isoxazolobenzoxazepine derivatives of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is in capsule, it may contain, in addition to materials of the above type, a liquid carrier such as a fatty oil. Other dosage unit forms may contain other various materials which modify the physical form of the dosage unit, for example as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the isoxazolobenzoxazepine derivative of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the isoxazolobenzoxazepine derivatives of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1

(a) 2-Fluoro-6-methoxymethoxybenzaldehyde oxime

3-Fluoromethoxymethoxybenzene (46.85 g, 0.30 mole) was dissolved in 400 ml of tetrahydrofuran (THF) and chilled to −75° C. n-Butyllithium (140 ml of 2.5 M, 0.35 mole) was added at a rate such that the internal reaction temperature did not rise above −65° C. After the addition was complete the reaction was stirred 30 minutes in the cold and then dimethylformamide (DMF) [27.0 ml, 25.5 g, 0.035 mole] was added. After an additional 30 minutes the reaction mixture was poured into $H_2O$ and extracted with ether. The combined organic phase was dried and concentrated under reduced pressure to give an oil. The oil was dissolved in 200 ml of pyridine, to which was then added 24.3 g of hydroxylamine hydrochloride (0.35 mole). This mixture was warmed on a steam bath for 30 minutes, swirling occasionally. At the end of this time the solvent was removed under reduced pressure and 1000 ml of $H_2O$ was added to the residue. The product crystallized rapidly under these conditions and was filtered off and washed well with $H_2O$. The wet product was taken up in $CH_2Cl_2$, dried with $MgSO_4$, and then isolated by evaporation of the solvent. Recrystallization from cyclohexane gave 2-fluoro-6-methoxymethoxybenzaldehyde oxime (47.5 g, 79%), m.p. 102°–104° C.

| ANALYSIS | | | |
| --- | --- | --- | --- |
| Calculated for $C_9H_{10}FNO_3$ | 54.27% C | 5.06% H | 7.03% N |
| Found | 54.33% C | 5.12% H | 6.95% N |

(b) 2-Fluoro-6-methoxymethoxybenzonitrile

2-Fluoro-6-methoxymethoxybenzaldehyde oxime of Example 1(a) (5.0 g, 0.025 mole) was dissolved in 50 ml of $CH_2Cl_2$ containing 6.9 ml of triethylamine (5.04 g, 0.05 mole). The reaction mixture was chilled to 5° C. and then trichloroacetyl chloride (4.55 g, 0.025 mole) was added dropwise in 20 ml of $CH_2Cl_2$. The cooling bath was removed and the reaction was brought to reflux. After 30 minutes an additional 2.0 g of trichloroacetyl chloride was added to the reaction mixture and refluxed was continued. After an additional 30 minutes the reaction mixture was poured into $H_2O$ and extracted with ether. The organic phase was washed three times with $H_2O$, dried, evaporated, and purified by flash chromatography (CH$_2$Cl$_2$). Obtained in this manner was 4.17 g (92%) of 2-fluoro-6-methoxymethoxybenzonitrile product. Recrystallization from pentane yielded 2-fluoro-6-methoxymethoxybenzonitrile, m.p. 53°–55° C.

| ANALYSIS | | | |
|---|---|---|---|
| Calculated for C$_9$H$_8$FNO$_2$ | 59.66% C | 4.45% H | 7.73% N |
| Found | 59.55% C | 4.47% H | 7.87% N |

(c) 2-[(Isopropylideneamino)oxy]-6-methoxymethoxybenzonitrile

Acetone oxime (11.14 g, 0.1524 mole) was dissolved in 300 ml of dry dimethyl formamide (DMF) and then potassium t-butoxide (17.0 g, 0.152 mole) was added portionwise. The reaction mixture was allowed to stir for 30 minutes at room temperature and the 2-fluoro-6-methoxymethoxybenzonitrile of Example 1(b) (23.0 g, 0.127 mole) was added in 150 ml of DMF. After 30 minutes the reaction mixture was poured into 1000 ml of water and stirred well as the product crystallized. The product was filtered off, washed well with water, and then taken up in CH$_2$Cl$_2$ and dried with magnesium sulfate. Concentration and recrystallization from methanol-water gave 20.5 g (69%) of 2-[(isopropylideneamino)oxy]-6-methoxymethoxybenzonitrile as fine needles, mp 62°–64° C.

| ANALYSIS | | | |
|---|---|---|---|
| Calculated for C$_{12}$H$_{14}$N$_2$O$_3$ | 61.52% C | 6.03% H | 11.96% N |
| Found | 61.29% C | 6.07% H | 11.49% N |

(d) 3-Amino-4-hydroxy-1,2-benzisoxazole

2-[(Isopropylidenamino)oxy]-6-methoxymethoxybenzonitrile of Example 1(c) (9.91 g, 0.0423 mole) was dissolved in 100 ml of methanol and then 100 ml of freshly prepared saturated HCl-ether was added. After stirring overnight (about 16 hours) at room temperature the reaction mixture was concentrated under reduced pressure and the residue triturated with CH$_2$Cl$_2$ and filtered. Recrystallization from methanol-water gave 5.62 g (89%) of 3-amino-4-hydroxy-1,2-benzisoxazole, mp 255° (d).

| ANALYSIS | | | |
|---|---|---|---|
| Calculated for C$_7$H$_6$N$_2$O$_2$ | 55.99% C | 4.03% N | 18.66% N |
| Found | 55.93% C | 4.01% N | 18.51% N |

(e) Methyl[(3-amino-1,2-benzisoxazol-4-yl)oxy]acetate

A mixture of 3-amino-4-hydroxy-1,2-benzisoxazole (17.5 g; 116.6 mmoles) of Example 1(d), potassium carbonate (19.4 g; 139.9 mmoles) and methyl bromoacetate (13.2 ml; 139.9 mmoles) in 225 ml acetone was refluxed for 2 hours. The reaction mixture was then added to a dilute aqueous HCl solution and extracted three times with ethyl acetate. The combined organics were dried (MgSO$_4$). The ester was purified via flash chromatography (10% ethyl acetate/dichloroethane) to give 11.3 g (43%) of a solid, mp 133°–139° C. A portion of this was recrystallized from methanol-water to give methyl[(3-amino-1,2-benzisoxazol-4-yl)oxy]acetate, mp 133°–139° C.

| ANALYSIS | | | |
|---|---|---|---|
| Calculated for C$_{10}$H$_{10}$N$_2$O$_4$ | 54.05% C | 4.54% H | 12.61% N |
| Found | 54.13% C | 4.61% H | 12.61% N |

(f) Isoxazolo[3,4,5-ef][1,4]benzoxazepin-4(5H)-one

A solution of methyl[(3-amino-1,2-benzisoxazol-4-yl)oxy]acetate (7.2 g; 32.2 mmoles) of Example 1(e) in 60 ml dimethylformamide (DMF) was added to a suspension of sodium hydride (1.9 g; 38.7 mmoles) in DMF. The reaction mixture was stirred for 20 minutes, then added to a dilute aqueous HCl solution, filtered and dried in vacuo to give 5.7 g (93%) of a solid, mp 188°–190° C. A portion of this was recrystallized from methanol to give isoxazolo[3,4,5-ef][1,4]benzoxazepin-4(5H)-one, mp 187°–189° C.

| ANALYSIS | | | |
|---|---|---|---|
| Calculated for C$_9$H$_6$N$_2$O$_3$ | 56.84% C | 3.18% H | 14.73% N |
| Found | 56.54% C | 3.01% H | 14.79% N |

EXAMPLE 2

3-Methylisoxazolo[3,4,5-ef][1,4]benzoxazepin-4(5H)-one

A solution of isoxazolo[3,4,5-ef][1,4]benzoxazepin-4(5H)-one (4.0 g; 21.0 mmoles) of Example 1(f) in 30 ml dimethylformamide (DMF) was added to a suspension of sodium hydride in DMF. The mixture was stirred for 15 minutes and iodomethane (1.4 ml; 23.1 mmoles) was added. The reaction mixture was then quenched into a dilute HCl solution, filtered, the resultant cake was washed with water and dried to give 3.34 g (78%) of a solid, mp 156°–159° C. This solid was recrystallized from methanol to give 2.1 g (48%) of 3-methylisoxazolo[3,4,5-ef][1,4]benzoxazepin-4(5H)-one, mp 158°–161° C.

| ANALYSIS | | | |
|---|---|---|---|
| Calculated for C$_{10}$H$_8$N$_2$O$_3$ | 58.82% C | 3.95% H | 13.72% N |
| Found | 58.71% C | 3.97% H | 13.73% N |

4,5-Dihydro-3-methylisoxazolo[3,4,5-ef][1,4]benzoxazepin-4-ol

To a cooled suspension of 3-methylisoxazolo[3,4,5-ef][1,4]benzoxazepin-4(5H)-one of Example 2 (5.54 g, 27.1 mmoles) in 100 ml tetrahydrofuran (THF) was added 27 ml of a 1 molar solution of lithium aluminum hydride in THF. After 15 minutes, the reaction mixture was quenched with 15 ml of a saturated NH$_4$Cl solution, diluted with ethyl acetate, filtered and dried (MgSO$_4$). The solution was then passed through a column of florisil (ethyl acetate) to give 3.95 g (71%) of a solid, mp 116°–119° C. This solid was recrystallized from ethyl acetate/hexane to give 2.95 g (53%) of 4,5-dihydro-3-methylisoxazolo[3,4,5-ef][1,4]benzoxazepin-4-o l, mp 118°–120° C.

| ANALYSIS | | | |
|---|---|---|---|
| Calculated for $C_{10}H_{10}N_2O_3$ | 58.25% C | 4.89% H | 13.59% N |
| Found | 58.05% C | 4.74% H | 13.40% N |

EXAMPLE 4

4,5-Dihydroisoxazolo[3,4,5-ef][1,4]benzoxazepin-4-ol

To a cooled solution of isoxazolo[3,4,5-ef][1,4]benzoxazepin-4(5H)-one of Example 1(f) 4,54 g, (23.9 mmoles) in 90 ml tetrahydrofuran was added 17 ml of a 1 molar solution of lithium aluminum hydride in THF. After 15 minutes, the reaction was quenched with 10 ml of a saturated NH4Cl solution, diluted with ethyl acetate, filtered and dried (MgSO4).

The desired compound was purified via flash chromatography (15% ethylacetate/dichloromethane) to give 2.5 g (54%) of a solid, m.p. 143°-147° C. This was recrystallized from ethyl acetate/hexane to give 1.94 g (42%) of 4,5-dihydroisoxazolo[3,4,5-ef][1,4]benzoxazepin-4-ol, m.p. =142.5°-144.5° C.

| ANALYSIS | | | |
|---|---|---|---|
| Calculated for $C_9H_8N_2O_3$ | 56.25% C | 4.20% H | 14.58% N |
| Found | 56.10% C | 4.24% H | 14.51% N |

EXAMPLE 5

4,5-Dihydro-3-(3-dimethylaminopropyl]isoxazolo[3,4,5-ef][1,4]benzoxazepine-4(5H)-one fumarate To a cooled solution of isoxazolo[3,4,5-ef][1,4]benzoxazepin-45H)-one of Example 1(f) (9.5 g; 50.0 mmoles) in 100 ml dimethylformamide was added to a suspension of NaH (50% in oil, washed twice with hexane, 2.93 g; 61.0 mmoles). To the resulting mixture was added dimethylaminopropyl chloride (7.3 g; 60.0 mmoles). The resultant mixture was heated at 65° C. for 17 hours. The reaction mixture was then added to water and extracted three times with ethyl acetate. The organics were washed with H2O and dried (saturated NaCl,MgSO4). The desired amine was purified via flash chromatography (4% methanol/dichloromethane) to give 7.5 g (54%) of an oil. A 3.27 g portion of the oil was dissolved in isopropanol and 1.1 equivalents of fumaric acid was added. After stirring for 6 hours, the salt was filtered and dried to give 4.34 g (51%) of 4,5-dihydro-3-(3-dimethylaminopropyl)isoxazolo[3,4,5-ef][1,4]benzoxazepin-4(5H)-one fumarate, mp 146°-149° C.

| ANALYSIS | | | |
|---|---|---|---|
| Calculated for $C_{14}H_{17}N_3O_3 \cdot C_4H_4O_4$ | 55.24% C | 5.54% H | 10.74% N |
| Found | 55.53% C | 5.47% H | 10.53% N |

EXAMPLE 6

4,5-Dihydro-3-methylisoxazolo[3,4,5-ef][1,4]benzoxazepine

To a solution of 3-methylisoxazolo[3,4,5-ef][1,4]benzoxazepin-4(5H)-one of Example 2 (4.84 g; 23.7 mmoles) in 200 ml tetrahydrofuran was added 72 ml of a 1 molar solution of a borane-tetrahydrofuran complex. After stirring for 3.5 hours at room temperature, an additional 24 ml of borane was added. This was stirred for 15 hours after which the reaction was quenched with 40 ml of a 10% NaOH solution. The aqueous was extracted three times with ethyl acetate and the combined organics were washed with water and dried (saturated NaCl, MgSO4). The amine was purified via flash chromatography (ethyl acetate/dichloromethane) to give 3.35 g (74%) of a solid, mp 95°-100° C. This was recrystallized from methanol/water to give 2.8 g (62%) of 4,5-dihydro-3-methylisoxazolo[3,4,5-ef][1,4]benzoxazepine, mp 98°-100° C.

| ANALYSIS | | | |
|---|---|---|---|
| Calculated for $C_{10}H_{10}N_2O_2$ | 63.15% C | 5.30% H | 14.73% N |
| Found | 63.15% C | 5.36% H | 14.73% N |

EXAMPLE 7

(a) 3-Amino-4-[(2-Bromoethyl)oxy]-1,2-benzisoxazole

3Amino-4-hydroxy-1,2-benzisoxazole (1.50 g, 0.010 mole) was dissolved in 75 ml of acetone to which was then added 10 ml of ethylene dibromide (21.8 g, 0.116 mole) and 2.0 g (0.014 mole) K2CO3. The reaction mixture was refluxed for 3 hours and then an additional 1.0 g K2CO3 was added and reflux was continued for 3 more hours. At the end of this time the reaction was distributed between 5% HCl and ethyl acetate and the organic phase was separated, dried, and concentrated under reduced pressure. Purification of the residue by flash chromatography (10% ethyl acetate-CH2Cl2) gave 1.55 g (60%) of product. Recrystallization from benzene yielded 3-amino-4-[(2-bromoethyl)oxy]-1,2-benzisoxazole, mp 105°-107° C.

| ANALYSIS | | | |
|---|---|---|---|
| Calculated for $C_9H_9BrN_2O_2$ | 42.04% C | 3.53% H | 10.90% N |
| Found | 42.01% C | 3.53% H | 10.95% N |

(b) 4,5-Dihydroisoxazolo[3,4,5-ef][1,4]benzoxazepine

3-Amino-4-[(2-bromoethyl)oxy]1,2-benzisoxazole of Example 7(a) (10.86 g, 0.0428 mole) was dissolved in 200 ml of tetrahydrofuran (THF) and 5.0 g of NaH (50% oil dispersion, 0.10 mole) was added. The reaction mixture was brought to reflux. After 30 minutes the reaction mixture was allowed to cool, an additional 1.0 g of NaH dispersion was added, and reflux was continued for 30 minutes. At the end of this time the reaction mixture was poured into H2O, acidified with concentrated hydrochloric acid, and the product extracted into ether. The organic phase was separated, dried, and concentrated, after which the residue was purified by flash chromatography (10% ethyl acetate -CH2Cl2). The material obtained in this manner retained a little yellow color, which was removed by dissolving the compound in CH2Cl2 and passing the solution over a short column of alumina. The product obtained in this manner after concentration of the solvent was recrystallized from CH2Cl2-pentane to give 2.20 g (29%) of 4,5-dihydroisoxazolo[3,4,5-ef][1,4]benzoxazepine, mp 165°-166° C.

| ANALYSIS: | | | |
|---|---|---|---|
| Calculated for $C_9H_8N_2O_2$: | 61.35% C | 4.58% H | 15.90% N |

-continued

ANALYSIS:

| Found: | 60.84% C | 4.89% H | 16.04% N |
|---|---|---|---|

EXAMPLE 8

4,5-Dihydro-3-(2-dimethylaminoethyl)isoxazolo[3,4,5-ef][1,4]benzoxazepine, sesquifumarate A solution of 4,5-dihydroisoxazolo[3,4,5-ef][1,4]benzoxazepine of Example 7(b) (3.9 g; 22.1 mmoles) in 60 ml dimethylformamide was added to a suspension of sodium hydride (1.3 g, 26.5 mmoles washed twice with hexane). This was followed by addition of dimethylaminoethyl chloride (2.6 g; 24.3 mmoles) and the mixture was heated at 70° C. for 2.5 hours. An additional 800 mg of the chloride was then added and this was heated for an additional 1 hour. The reaction was then added to a dilute HCl solution and this was washed twice with ethyl acetate. The aqueous phase was then basified with 50% NaOH and extracted twice with ethyl acetate. The combined organics were washed once with water and dried (saturated NaCl, MgSO$_4$) to give 4.1 g (75%) of an oil. This oil was dissolved in 60 ml isopropanol and 2.8 g (1.5 eq.) of fumaric acid was added. The resulting salt was crystallized with ethyl ether, collected and recrystallized from ethyl acetate: ethanol to give 3.94 g (42%) of 4,5-dihydro-3-(2-dimethylaminoethyl)isoxazolo[3,4,5-ef][1,4]benzoxazepine, sesquifumarate, mp 102°–106° C.

ANALYSIS:

| Calculated for $C_{13}H_{17}N_3O_2.1.5C_4H_4O_4$: | 54.15% C | 5.50% H | 9.97% N |
|---|---|---|---|
| Found: | 54.54% C | 5.80% H | 9.97% N |

EXAMPLE 9

3-(2-Phthalimidoethyl)isoxazolo[3,4,5-ef][1,4]benzoxazepin-4(5H)-one

A solution of isoxazolo[3,4,5-ef][1,4]benzoxazepin-4(5H)-one of Example 1(f) (5.5 g; 28.9 mmoles) in 65 ml dimethylformamide was added to a suspension of NaH (1.8 g; 37.6 mmoles) in DMF. This was followed by the addition of 2-bromoethylphthalimide (8.1 g; 31.8 mmole). The reaction was heated at 75° C. for 2 hours, then quenched into water. The resulting solid was filtered, dried and recrystallized from dimethylformamide/water to give 5.62 g (54%) of 3-(2-phthalimidoethyl)isoxazolo[3,4,5-ef][1,4]benzoxazepin-4(5H)-one, mp 197.5°–199° C.

ANALYSIS:

| Calculated for $C_{19}H_{13}N_3O_5$: | 62.81% C | 3.61% H | 11.57% N |
|---|---|---|---|
| Found: | 62.74% C | 3.60% H | 11.42% N |

EXAMPLE 10

(S)-4,5-Dihydro-3-[(1-methyl-2-pyrrolidinyl)methyl]isoxazolo[3,4,5-ef][1,4]benzoxazepine, fumarate, hemi-hydrate To a suspension of NaH (3.1 g; 64.5 mmoles, washed twice with hexane) in dimethylformamide was added a solution of 4,5-dihydroisoxazolo[3,4,5-ef][1,4]benzoxazepine of Example 7(b) (4.55 g; 25.8 mmoles) in 65 ml DMF. This was stirred for 15 minutes and a solution of excess (S)-1-methyl-2-chloromethylpyrrolidone hydrochloride in 70 ml DMF was added. The reaction was stirred at 70° C. for 5 hours, then quenched into a dilute HCl solution. This was washed twice with ethyl acetate and then basified with 50% NaOH. This aqueous was extracted three times with ethyl acetate and then the combined organics were washed with water and dried (saturated NaCl, MgSO$_4$). The amine was purified via flash chromatography (3.5% methano/dichloromethane) to give 2.89 g of an oil. This was dissolved in diethyl ether and an ether solution of fumaric acid was added. The resultant solid was triturated several times with ether and filtered to give 2.5 g of (S)-4,5-dihydro-3-[(1-methyl-2-pyrrolidinyl)methyl]isoxazolo [3,4,5-ef][1,4]benzoxazepine, fumarate, hemi-hydrate, mp 115°–120° C.

ANALYSIS:

| Calculated for $C_{15}H_{19}N_3O_2.C_4H_4O_4.0.5H_2O$: | 57.27% C | 6.02% H | 10.55% N |
|---|---|---|---|
| Found: | 57.68% C | 5.92% H | 10.45% N |

EXAMPLE 11

4,5-Dihydro-3-methylaminocarbonylisoxazolo[3,4,5-ef][1,4]benzoxazepine

A solution of 4,5-dihydroisoxazolo[3,4,5-ef][1,4]benzoxaxepine of Example 7(b) (3.7 g; 21.0 mmole) in 60 ml dimethylformamide (DMF) was added to a suspension of sodium hydride (1.2 g; 25.2 mmole) in DMF. After 15 minutes, a solution of methylisocyanate in 15 ml DMF was added. The reaction was quenched into a dilute solution of HCl and extracted thrice with ethyl acetate. The organics were washed with water and dried (saturated NaCl solution, MgSO$_4$). The desired urea was purified via flash chromatography (6% ethylacetate/dichloromethne) to give a solid which was triturated with pentane to give 2.4 g (49%) of 4,5-dihydro-3-methylaminocarbonylisoxazolo [3,4,5-ef][1,4]benzoxazepine, mp 177°–179.5° C.

ANALYSIS:

| Calculated for $C_{11}H_{11}N_3O_3$: | 56.65% C | 4.76% H | 18.02% N |
|---|---|---|---|
| Found: | 56.27% C | 4.79% H | 18.20% N |

EXAMPLE 12

8-[4-(4,5-dihydro-4-oxoisoxazolo[3,4,5-ef][1,4]benzoxazepin-3-yl)butyl]-8-azaspiro[4,5]decan-7,9-dione To a suspension of sodium hydride (1.1 g;21.8 mmoles, washed once with hexane) in dimethylformamide was added a solution of isoxazolo [3,4,5-ef][1,4]benzoxazepin-4(5H)-one of Example 1(f) (3.45 g; 18.1 mmoles) in 60 ml DMF. 8-[4-(4-methylbenzenesulfonyloxy)butyl]-8-azaspiro[4,5]decan- 7,9-dione was added thereto after 5 minutes and the reaction was heated at 100° C. for ½ hour. The reaction mixture was then quenched into a dilute HCl solution and extracted three times with ethyl acetate. The organics were washed with water and dried (MgSO$_4$). This was concentrated to an oil which was triturated with ethyl ether/hexane to give 3.53 g (47%) of a powder, mp 113°–117° C. The solid was recrystallized from methanol/water to give 3.26 g(44%) of 8-[4-(4,5-dihydro-4-oxoisoxazolo[3,4,5-ef][1,4]benzoxazepin-3-yl)butyl]-8-azaspiro[4,5]decan-7,9-dione, mp 116°–118° C.

| ANALYSIS: | | | |
|---|---|---|---|
| Calculated for C22H25N3O5: | 64.22% C | 6.12% H | 10.21% N |
| Found: | 64.44% C | 6.25% H | 10.29% N |

EXAMPLE 13

4,5-Dihydro-3-(2-methylaminoethyl)isoxazolo[3,4,5-ef][1,4]benzoxazepine hydrochloride A mixture of 4,5-dihydro-3-(2-dimethylaminoethyl)isoxazolo[3,4,5-ef][1,4]benzoxazepine of Example 8(9.65 g; 39.0 mmoles),-chloroethylchloroformate(4.8 ml; 39.0 mmoles) and 0.5 ml triethylamine in 100 ml 1,2-dichloroethane was refluxed for 10 minutes. The solvent was removed in vacuo and the resulting carbamate was purified via flash chromatography (ethyl acetate/dichloromethane) to give 10.4 g of an oil which was used without further purification. The carbamate was dissolved in 100 ml methanol and refluxed for 15 minutes, after which the solvent was concentrated in vacuo to give 7.5 g (71%) of a solid, mp 196°–202° C. A 3.2 g portion of this was recrystallized from methanol/diethyl ether to give 2.72 g (61%) of 4,5-dihydro-3-(2-methylaminoethyl)isoxazolo[3,4,5-ef][1,4]benzoxazepine hydrochloride, mp 199°–101° C.

| ANALYSIS: | | | |
|---|---|---|---|
| Calculated for C12H15N3O2.HCl: | 53.43% C | 5.98% H | 15.58% N |
| Found: | 53.05% C | 6.21% H | 15.62% N |

EXAMPLE 14

4,5-Dihydro-3-[2-(N-methyl-N-(4-(8-aza-7,9-dioxospiro[4,5]dec an-8-yl)butyl)amino)ethyl]isoxazolo[3,4,5-ef][1,4]benzoxazepine, sesquifumarate A mixture of 4,5-dihydro-3-(2-methylaminoethyl)isoxazolo[3,4,5-ef]benzoxazepine of Example 13(3.7 g; 1.59 mmoles), potassium carbonate (2.6 g; 19.1 mmoles) and 8-[4-(4-methylbenzenesulfonyloxy)butyl]-8-azaspiro[4,5]decan-7,9-dione (6.9 g; 17.4 mmoles) in 100 ml dimethylformamide was heated at 80° C. for 17 hours. The reaction was added to water and extracted twice with ethyl acetate. The combined organics were washed with water and dried saturated NaCl,MgSO4. The amine was purified via flash chromatography (5% methanol/dichloromethane) to give 2.95 g (41%) of an oil. This oil was dissolved in isopropanol and an equivalent of fumaric acid was added. The solvent was concentrated off and the resulting gummy solid was triturated with ethyl ether to give 2.45 g (24%) of a powder, mp 118°–123° C. This was recrystallized from ethyl acetate to give 2.11 g (21%) of 4,5-dihydro-3-[2-(N-methyl-N-(4-(8aza-7,9-dioxospiro[4,5]dec an-8-yl)butyl)amino) ethyl]isoxazolo[3,4,5-ef][1,4]benzoxazepine, sesquifumarate, mp 120°–123° C.

| ANALYSIS: | | | |
|---|---|---|---|
| Calculated for C25H34N4O4.1.5C4H4O4: | 59.29% C | 6.40% H | 8.90% N |
| Found: | 59.29% C | 6.44% H | 8.86% N |

EXAMPLE 15

4,5-Dihydro-3-(4,4-diphenylbutyl)isoxazolo[3,4,5-ef][1,4]benzoxazepine

To a suspension of sodium hydride (50% in oil; 1.1 g; 21.6 mmoles; washed with hexane) in dimethylformamide was added a solution of 4,5-dihydroisoxazolo[3,4,5-ef][1,4]benzoxazepine of Example 7(b) (3.17 g; 18.0 mmoles) in 100 ml DMF. This was followed by addition of 4-methanesulfonyloxy-1,1-diphenylbutane(6.1 g; 19.8 mmoles) and the reaction was heated at 90° C. for 4 hours. The reaction was quenched into water and the aqueous phase was extracted thrice with ethyl acetate. The combined organics were washed with water and dried (MgSO4). The amine was purified via flash chromatography (dichloromethane) to give 5.13 g (74%) of a solid, mp 88°–89° C. This was recrystallized from methanol to give 3.60 g (52%) of 4,5-dihydro-3-(4,4-diphenylbutyl)isoxazolo[3,4,5-ef][1,4]benzoxazepine, mp 99°–102° C.

| ANALYSIS: | | | |
|---|---|---|---|
| Calculated for C25H24N2O2: | 78.10% C | 6.29% H | 7.29% N |
| Found: | 78.26% C | 6.38% H | 7.36% N |

EXAMPLE 16

4,5-Dihydro-3-(2-propynyl)isoxazolo[3,4,5-ef][1,4]benzoxazepine

A solution of 4,5-dihydroisoxazolo[3,4,5-ef][1,4]benzoxazepine of Example 7(b) (3.9 g; 22.1 mmoles) in 120 ml dimethylformamide was added to a suspension of sodium hydride (1.4 g; 27.7 mmoles). This was followed by a solution of propargyl bromide (2.7 ml of 80% solution; 24.4 mmoles). The reaction was heated at 80° C. for 1.5 hours and then quenched into water (400 ml). The resulting precipitate was filtered, rinsed and dried, then passed through a column of florisil (ethyl acetate/dichloromethane). This gave 3.5 g of a solid, mp 100°–104° C., which was recrystallized from isopropanol to give 2.5 g (53%) of 4,5-dihydro-3-(2-propynyl)isoxazolo[3,4,5-ef][1,4]benzoxazepine, mp 104°–106° C.

| ANALYSIS: | | | |
|---|---|---|---|
| Calculated for C12H10N2O2: | 67.28% C | 4.71% H | 13.08% N |
| Found: | 67.21% C | 4.68% H | 13.14% N |

EXAMPLE 17

4,5-Dihydro-3-(3-dimethylaminopropyl)isoxazolo[3,4,5-ef][1,4]benzoxazepine sesquifumarate A solution of 3-(3-dimethylaminopropyl)isoxazolo[3,4,5-ef].[1,4]benzoxazepin-4(5H)-one free base of Example 5 (3.91 g; 14.2 mmoles) in 175 ml tetrahydrofuran was treated with 43 ml of a 1 molar solution of borane in tetrahydrofuran. This was stirred at ambient temperature for 20 hours, at which time the borane was quenched with 30 ml of 10% NaOH. The resulting bilayer was separated; the organic layer was diluted with ethyl acetate and extracted three times with dilute HCl solution. This aqueous phase was washed with ethyl acetate, then basified with 50% NaOH and extracted thrice with ethyl acetate. The combined organics were washed with water, dried (MgSO$_4$) and concentrated to an oil. The amine was dissolved in 20 ml isopropanol and treated with 1.1 equivalents of fumaric acid and the resulting salt was crystallized out with ethyl ether to give 1.85 g (30%) of 4,5-dihydro-3-(3-dimethylaminopropyl)isoxazolo[3,4,5-ef][1,4]benzoxazepine, sesquifumarate, mp 106°–109° C.

| ANALYSIS: | | | |
|---|---|---|---|
| Calculated for $C_{14}H_{19}N_3O_2 \cdot 1.5C_4H_4O_4$: | 55.17% C | 5.79% H | 9.65% N |
| Found: | 54.80% C | 5.72% H | 9.63% N |

EXAMPLE 18

4,5-Dihydro-3-(3-dimethylaminopropyl)isoxazolo[3,4,5-ef][1,4]benzoxazepine, hydrochloride, hemi-hydrate A solution of 4,5-dihydro-3-(3-dimethylaminopropyl)isoxazolo[3,4,5-ef][1,4]benzoxazepine, of Example 17 (15.2 g; 58.2 mmoles) and 1-chloroethylchloroformate (7.1 ml; 58.2 mmoles) in 150 ml of 1,2-dichloroethane was refluxed for 2 hours. The solvent was evacuated in vacuo and the carbamate was purified via flash chromatography (ethyl acetate/dichloromethane) to give 11.0 g of an oil. The carbamate was dissolved in 150 ml methanol, refluxed for 20 minutes, and the solvent was evacuated in vacuo to give, after trituration with ether, 7.56 g (44%) of powder. A 3.5 g portion of this was recrystallized from methanol:diethyl ether to give 2.78 g (35% yield) of 4,5-dihydro-3-(3-dimethylaminopropyl)isoxazolo[3,4,5-ef][1,4]benzoxazepine, hydrochloride, hemi-hydrate, mp 155°–157° C.

| ANALYSIS: | | | |
|---|---|---|---|
| Calculated for $C_{13}H_{17}N_3O_2 \cdot HCl \cdot 0.5H_2O$: | 55.33% C | 6.54% H | 14.35% N |
| Found: | 53.53% C | 6.19% H | 14.39% N |

EXAMPLE 19

3-(2-Propynyl)isoxazolo[3,4-ef][1,4]benzoxazepin-4(5H)-one

A solution of isoxazolo[3,4,5-ef][1,4]benzoxazepin-4(5H)-one of Example 1(f) (11.7 g; 61.5 mmoles) in 180 ml dimethylformamide was added to a suspension of sodium hydride (3.5 g; 73.8 mmoles) in DMF. After 15 minutes, an 80% weight solution of propargyl bromide in toluene was added (7.5 ml; 67.7 mmoles). The reaction mixture was added to an iced HCl solution and the resulting precipitate was filtered, rinsed with water and dried. The compound was then passed through a packing of silica gel (ethyl acetate) to give 9.50 g (68%) of a powder, mp 131°–141° C. A 3.86 g portion of this was recrystallized from methanol to give 2.37 g (42%) of 3-(2-propynyl)isoxazolo[3,4-ef][1,4]benzoxazepin-4(5H)-one, mp 142°–145° C.

| ANALYSIS: | | | |
|---|---|---|---|
| Calculated for $C_{12}H_8N_2O_3$: | 63.16% C | 3.53% H | 12.18% N |
| Found: | 63.23% C | 3.64% H | 12.26% N |

EXAMPLE 20

3-(4-Pyrrolidinyl-2-butynyl)isoxazolo[3,4,5-ef][1,4]benzoxazepin-4(5H)-one

A mixture of 3-(2-propynyl)isoxazolo[3,4-ef][1,4]benzoxazepin-4(5H)-one(3.09 g; 13.5 mmoles)-pyrrolidine (1.3 ml, 14.9 mmoles), paraformaldehyde (1.7 g) and cuprous chloride (100 mg) in 100 ml 1,4-dioxane was heated on a steam bath for 5 minutes. The mixture was then diluted with ethyl acetate, filtered through celite and concentrated. The amine was purified via flash chromatography (5% methanol/dichloromethane) to give 3.3 g (79%) of a solid, mp 74°–81° C. This was recrystallized from cyclohexane to give 2.35 g (56%) of 3-(4-pyrrolidinyl-2-butynyl)isoxazolo[3,4,5-ef][1,4]benzoxazepin-4(5H)-one, mp 83°–85° C.

| ANALYSIS: | | | |
|---|---|---|---|
| Calculated for $C_{17}H_{17}N_3O_3$: | 65.60% C | 5.51% H | 13.50% N |
| Found: | 65.59% C | 5.45% H | 13.35% N |

EXAMPLE 21

3-(4-Piperidinyl-2-butynyl)isoxazolo[3,4,5-ef][1,4]benzoxazepin-4(5H)-one

A mixture of 3-(2-propynyl)isoxazolo[3,4,5-ef][]1,4]benzoxazepin-4(5H)-one (3.2 g; 14 mmoles) paraformaldehyde (1.5 g) and cuprous chloride (100 mg) in 100 ml 1,4-dioxane was heated on a steam bath for 20 minutes. The reaction was diluted with ethyl acetate and filtered through celite. The filtrate was then passed through a column of florisil (ethyl acetate) which gave 3.7 g (81%) of a solid, mp 90°–92° C. This was recrystallized from cyclohexane to give 2.12 g (47%) of 3-(4-piperidinyl-2-butynyl)isoxazolo[3,4,5-ef][1,4]benzoxazepin-4(5H)-one, mp 92°–94° C.

| ANALYSIS: | | | |
|---|---|---|---|
| Calculated for $C_{18}H_{19}N_3O_3$: | 66.45% C | 5.89% H | 12.92% N |
| Found: | 66.40% C | 5.87% H | 12.91% N |

EXAMPLE 22

4,5-Dihydro-3-[3-(N-methyl-N-(4-(8-aza-7,9-dioxopiro[4,5]decan—8-yl)butyl)amino)propyl]isoxazolo[3,4,5-ef][1,4]benzoxazepine, hydrochloride, hemihydrate To a suspension of sodium hydrate (760 mg; 15.8 mmoles) in dimethylformamide was added a solution of 4,5-dihydro-3-(3-methylaminopropyl)isoxazolo[3,4,5-ef][1,4]benzoxazepine of Example 18 (3.25 g; 13.1 mmoles) in 100 ml DMF. This was followed by the addition of 8-[4-(4-methylbenzenesulfonyloxy)butyl]-8-azaspiro[4,5]decan-7,9-dione (5.7 g; 14.5 mmoles). The reaction was heated for 4 hours at 80° C. and then quenched into water and extracted twice with ethyl acetate. The combined organics were washed with water and dried (MgSO$_4$). The amine was purified via flash chromatography (5% methanol/dichloromethane) to give 3.4 g (55%) of oil. After attempted purification via the fumarate, the hydrochloride was formed and triturated in ethyl ether for 5 days to give 1.9 g (28%) of 4,5-dihydro-3-3-[6-(N-methyl-N-(4-(8-aza-7,9-dioxospiro[4,5]decan-8-yl)butyl)amino)propyl]isoxazolo(3,4,5-ef][1,4]benzox az epine, hydrochloride, hemihydrate, mp 128°–134° C.

| ANALYSIS: | | | |
|---|---|---|---|
| Calculated for C$_{26}$H$_{36}$N$_4$O$_4$.HCl.0.5H$_2$O: | 60.74% C | 7.45% H | 10.90% N |
| Found: | 60.67% C | 7.41% H | 10.87% N |

EXAMPLE 23

3-[4-(Phenylpiperidinyl)-2-butynyl]isoxazolo[3,4,5-ef][1,4]benzoxazepin-4(5H)-one A mixture of 3-(2-propynyl)isoxazolo[3,4,5-ef][1,4]benzoxasepin-4(5H)-one of Example 19 (3.9 g, 17.1 mmoles), 4-phenylpiperidine (2.76 g, 17.1 mmoles), paraformaldehyde (1.68 g) and cuprous chloride (100 mg) was heated on a steam bath for 25 minutes. The reaction was diluted with ethyl acetate filtered thru celite, then passed through a column of florasil (ethylacetate). This gave 5.8 g (84%) of a solid which was recrystallized from methanol to give 3.15 g (46%) of 3-[4-(phenylpiperidinyl)-2-butynyl]isoxazolo[3,4,5-ef][1,4]benzoxazepin-4(5H)-one, mp 140°–142° C.

| ANALYSIS: | | | |
|---|---|---|---|
| Calculated for C$_{24}$H$_{23}$N$_3$O$_3$: | 71.80% C | 5.77% H | 10.47% N |
| Found: | 71.72% C | 5.74% H | 10.56% N |

EXAMPLE 24

(a) [(3-Amino-1,2-benzisoxazol-4-yl)oxy]acetonitrile

To a suspension of 3-amino-4-hydroxy-1,2-benzoxazole of Example 1(d) (4.2 g; 27.9 mmoles) in 80 ml acetone was added K$_2$CO$_3$ (4.6 g; 33.5 mmoles) and chloroacetonitrile (1.9 ml; 30.0 mmoles). This was refluxed for 5 hours after which the reaction was quenched with dilute HCl and extracted thrice with ethyl acetate. The combined organics were washed with water and dried (saturated NaCl,MgSO$_4$). The compound was then passed thru a column of florisil (ethyl acetate) to give 3.7 g (70%) of a solid. This was recrystallized from methanol to give 2.17 g (41%) of [(3-amino-1,2-benzisoxazol-4-yl)oxy]acetonitrile, mp 133°–136° C.

| ANALYSIS: | | | |
|---|---|---|---|
| Calculated for C$_9$H$_7$N$_3$O$_2$: | 57.14% C | 3.73% H | 22.21% N |
| Found: | 56.96% C | 3.64% H | 22.14% N |

(b) 3-(Phenylmethyl)isoxazolo[3,4,5-ef][1,4]benzoxazepin-4(5H)-one

To a suspension of NaH (1.3 g; 26.9 mmoles) in 6 ml dimethylformamide was added a solution of [(3-amino-1,2-benzisoxazol-4-yl)oxy]acetonitrile of Example 24(a) (4.25 mmoles) in 65 ml DMF. This was followed by the addition of benzyl bromide (2.9 ml; 24.7 mmoles. The reaction was quenched into a dilute HCl solution and extracted three times with ethyl acetate. The organics were washed with water and dried (saturated NaCl, MgSO$_4$). The product was purified via flash chromatography (dichloromethane/hexane, 2:1) to give a solid which was recrystallized from isopropyl ether to give 2.2 g (35%) of 3-(phenylmethyl)isoxazolo[3,4,5-ef][1,4]benzoxazepin-4(5H)-one, mp 105°–107° C.

| ANALYSIS: | | | |
|---|---|---|---|
| Calculated for C$_{16}$H$_{12}$N$_2$O$_3$: | 68.56% C | 4.32% H | 10.00% N |
| Found: | 68.69% C | 4.23% H | 10.09% N |

EXAMPLE 25

Isoxazolo[3,4,5-ef][1,4]benzoxazepin-4(5H)-imine

A solution of [(3-amino-1,2-benzisoxazol-4-yl)oxy]acetonitrile of Example 24(a) (4.44 g; 23.5 mmoles) in 40 ml dimethylformamide was added to a suspension of sodium hydride (50% in oil, washed twice with hexane) in DMF. After 15 minutes, the reaction was added to water, rinsed with water and dried to give 3.4 g of a powder. This was recrystallized from dimethylsulfoxide/water to give 2.85 g (64%) of isoxazolo[3,4,5-ef][1,4]benzoxazepin-4(5H)-imine, mp 273°–276° C.

| ANALYSIS: | | | |
|---|---|---|---|
| Calculated for C$_9$H$_7$N$_3$O$_2$: | 57.14% C | 3.73% H | 22.21% N |
| Found: | 57.07% C | 3.90% H | 21.77% N |

We claim:
1. An isoxazolobenzoxazepine of the formula

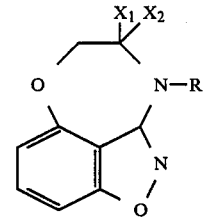

wherein X$_1$ is H; X$_2$ is H or OH; or X$_1$ and X$_2$ taken together are carbonyl oxygen or

NH;

R is (1) H, (2) loweralkyl, (3) arylloweralkyl, (4) loweralkynyl, (5) loweralkenyl, (6) -loweralkylene —N<R_1 / R_2, 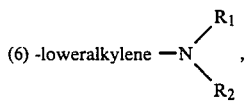

where $R_1$ and $R_2$ are independently (a) H, (b) lower alkyl, (c) arylloweralkyl, (d) lower alkylene —N<...>—(Z)_n, 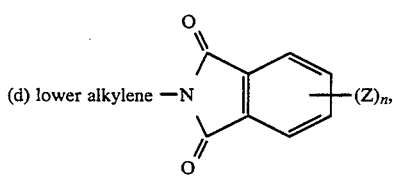

where Z is H, halogen, loweralkyl, loweralkoxy, $CF_3$, nitro or amino and n is an integer of 1 to 3;

(e) -loweralkylene —N<...>(CH_2)_{n''}, 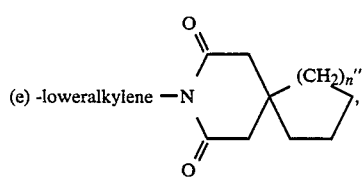

where n" is an integer of 1 to 3; or (f) $R_1$ and $R_2$ taken together with the nitrogen atom are substituted or unsubstituted piperidino or pyrrolidino of the formula —N<(CH_2)_m / (CH_2)_2>CHR_3 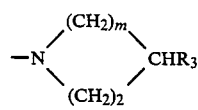

where $R_3$ is H, loweralkyl or aryl, and m is an integer of 1 or 2;

(7) loweralkylene —CH_2<N—R_4 / (CH_2)_{m'}> where $R_4$ is H or loweralkyl and m' is an integer of 3 or 4;

(8) -lower alkylene —N<...>—(Z)_n; 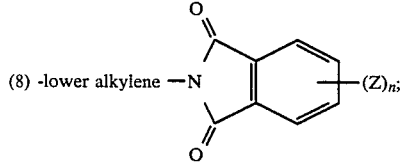

where Z and n are as previously defined;

(9) -loweralkylene —N<...>(CH_2)_{m'''}, 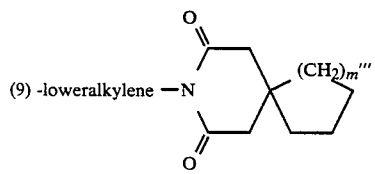

where m''' is an integer of 1, 2 or 3;

(10) loweralkynyl —N<R_5 / R_6 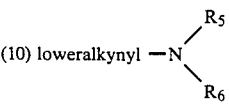

where $R_5$ and $R_6$ are independently alkyl, aryl lower alkyl or are taken together with the N atom to form a substituted or unsubstituted piperidino or pyrrolidino group of the formula —N<(CH_2)_m / (CH_2)_2>—R_3, 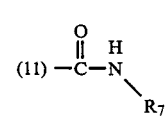

where $R_3$ and m are as defined above;

(11) —C(=O)—N<H / R_7 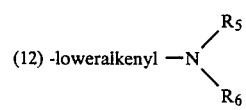

where $R_7$ is loweralkyl, aryl, or aryl loweralkyl;

(12) -loweralkenyl —N<R_5 / R_6 where $R_5$ and $R_6$ are as previously defined; and the pharmaceutically acceptable acid addition salts thereof and where applicable to the geometric, and stereo isomers thereof.

2. The compound as defined in claim 1 wherein R is lower alkyl or aryl lower alkyl when $X_1$ and $X_2$ are H.

3. The compound as defined in claim 1 wherein R is lower alkyl or aryl lower alkyl when $X_1$ is OH and $X_2$ is H.

4. The compound as defined in claim 1 which is isoxazolo[3,4,5-ef][1,4]benzoxazepin-4(5H)-one and the pharmaceutically acceptable addition salts thereof.

5. The compound as defined in claim 1 which is 3-methylisoxazolo[3,4,5-ef][1,4]benzoxazepin-4(5H)-one and the pharmaceutically acceptable addition salts thereof.

6. The compound as defined in claim 1 which is 4,5-dihydro-3-methylisoxazolo[3,4,5-ef][1,4]benzoxazepin-4-ol and the pharmaceutically acceptable addition salts thereof.

7. The compound as defined in claim 1 which is 4,5-dihydroisoxazolo[3,4,5-ef][1,4]benzoxazepin-4-ol and the pharmaceutically acceptable addition salts thereof.

8. The compound as defined in claim 1 which is 3-(3-dimethylaminopropyl)isoxazolo[3,4,5-ef][1,4]benzoxazepin-4(5H)-one and the pharmaceutically acceptable addition salts thereof.

9. The compound as defined in claim 8 wherein the acid addition salt is the fumarate.

10. The compound as defined in claim 1 which is 4,5-dihydro-3-methylisoxazolo[3,4,5-ef][1,4]benzoxazepine and the pharmaceutically acceptable addition salts thereof.

11. The compound as defined in claim 1 which is 4,5-dihydroisoxazolo[3,4,5-ef][1,4]benzoxazepine and the pharmaceutically acceptable addition salts thereof.

12. The compound as defined in claim 1 which is 4,5-dihydro-3-(2-dimethylaminoethyl)isoxazolo[3,4,5-ef][1,4]benzoxazepine and the pharmaceutically acceptable addition salts thereof.

13. The compound as defined in claim 12 wherein the acid addition salt is the sesquifumarate.

14. The compound as defined in claim 1 which is 4,5-dihydro-3-(4,4-diphenylbutyl)isoxazolo[3,4,5-ef][1,4]benzoxazepine and the pharmaceutically acceptable addition salts thereof.

15. The compound as defined in claim 1 which is isoxazolo[3,4,5-ef][1,4]benzoxazepin-4(5H)-imine and the pharmaceutically acceptable addition salts thereof.

16. The compound as defined in claim 1 which is 3-(phenylmethyl)isoxazolo[3,4,5-ef][1,4]benzoxazepin-4(5H)-one and the pharmaceutically acceptable addition salts thereof.

17. The compound as defined in claim 1 which is 4,5-dihydro-3-(3-dimethylaminopropyl)isoxazolo[3,4,5-ef][1,4]benzoxazepine and the pharmaceutically acceptable addition salts thereof.

18. The compound as defined in claim 17 wherein the acid addition salt is the sesquifumarate.

19. The compound as defined in claim 1 which is 4,5-dihydro-3-(2-methylaminoethyl)isoxazolo[3,4,5-ef][1,4]benzoxazepine and the pharmaceutically acceptable addition salts thereof.

20. The compound as defined in claim 19 wherein the acid addition salt is the hydrochloride.

21. The compound as defined in claim 1 which is 4,5-dihydro-3-(2-propynyl)isoxazolo[3,4,5-ef][1,4]benzoxazepine and the pharmaceutically acceptable addition salts therein.

22. The compound as defined in claim 1 which is 3-(2-propynyl)isoxazolo[3,4,5-ef][1,4]benzoxazepin-4(5H)-one and the pharmaceutically acceptable addition salts thereof.

23. The compound as defined in claim 1 which is 3-(4-piperidinyl-2-butynyl)isoxazolo[3,4,5-ef][1,4]benzoxazepin-4(5H)-one and the pharmaceutically acceptable addition salts thereof.

24. The compound as defined in claim 1 which is 3-(4-pyrrolidinyl-2-butynyl)isoxazolo[3,4,5-ef][1,4]benzoxazepin-4(5H)-one and the pharmaceutically acceptable addition salts thereof.

25. The compound as defined in claim 1 which is 4,5-dihydro-3-(3-methylaminopropyl)isoxazolo[3,4,5-ef][1,4]benzoxazepine and the pharmaceutically acceptable addition salts thereof.

26. The compound as defined in claim 25 which is 4,5-dihydro-3-(3-methylaminopropyl)isoxazolo[3,4,5-ef][1,4]benzoxazepine hydrochloride, hemihydrate.

27. The compound as defined in claim 1 which is 4,5-dihydro-3[(1-methyl-2-pyrrolidinyl)methyl]isoxazolo[3,4,5-ef][1,4]benzoxazepine and the pharmaceutically acceptable addition salts thereof.

28. The compound as defined in claim 27 which is (S)-4,5-dihydro-3-[(1-methyl-2-pyrrolidinyl)methyl]isoxazolo[3,4,5-ef][1,4]benzoxazepine, fumarate, hemihydrate.

29. The compound as defined in claim 1 which is 4,5-dihydro-3-methylaminocarbonylisoxazolo[3,4,5-ef][1,4]benzoxazepine and the pharmaceutically acceptable addition salts thereof.

30. The compound as defined in claim 1 which is 4,5-dihydro-3-[2-(N-methyl-N-(4-(8-azaspiro[4,5]decan-7,9-dione)butyl)amino)ethyl]isoxazolo-[3,4,5-ef][1,4]benzoxazepine and the pharmaceutically acceptable addition salts thereof.

31. The compound as defined in claim 30 wherein the addition salt is the sesquifumarate.

32. The compound as defined in claim 1 which is 4,5-dihydro-3-[3-(N-methyl-N-(4-(8-azaspiro[4,5]decan-7,9-dione)butyl)amino)propyl]isoxazolo[3,4,5-ef][1,4]benzoxazepine and the pharmaceutically acceptable addition salts thereof.

33. The compound as defined in claim 32 which is 4,5-dihydro-3-[3-(N-methyl-N-(4-(8-azaspiro[4,5]decan-7,9-dione)butyl amino)propyl]isoxazolo[3,4,5-ef][1,4]benzoxazepine, hydrochloride, hemihydrate.

34. The compound as defined in claim 1 which is 3-(2-phthalimidoethyl)isoxazolo[3,4,5-ef][1,4]benzoxazepin-4(5H)-one and the pharmaceutically acceptable addition salts thereof.

35. The compound as defined in claim 1 which is 8-[4-(4,5-dihydro-4-oxoisoxazolo[3,4,5-ef][1,4]benzoxazepin-3-yl)butyl]-8-azaspiro[4,5]decan-7,9-dione and the pharmaceutically acceptable addition salts thereof.

36. The compound as defined in claim 1 which is 3-[4-(4-phenylpiperidinyl)-2-butynyl]-isoxazolo[3,4,5-ef][1,4]benzoxazepin-4(5H)-one and the pharmaceutically acceptable addition salts thereof.

37. An analgesic composition which comprises an effective pain alleviating amount of an active ingredient having the formula

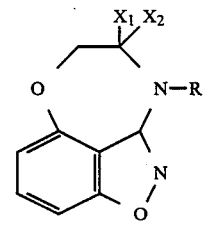

wherein $X_1$ is H; $X_2$ is H or OH; or $X_1$ and $X_2$ taken together are carbonyl oxygen or

R is (1) H, (2) loweralkyl, (3) arylloweralkyl, (4) (5) loweralkenyl,

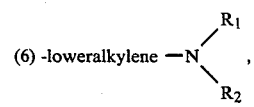

where $R_1$ and $R_2$ are independently (a) H, (b) lower

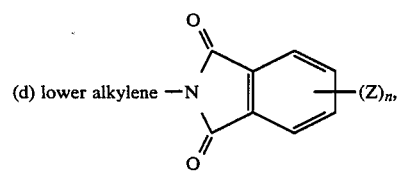

alkyl, (c) arylloweralkyl, (d)

(d) lower alkylene 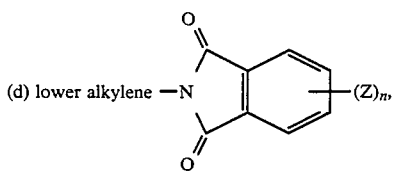

where Z is H, halogen, loweralkyl, loweralkoxy, $CF_3$, nitro or amino and n is an integer of 1 to 3;

(e) -loweralkylene 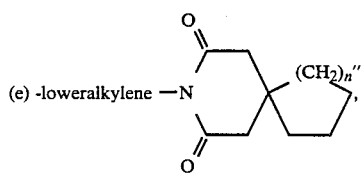

where n" is an integer of 1 to 3; or (f) $R_1$ and $R_2$ taken together with the nitrogen atom are substituted or unsubstituted piperidino or pyrrolidino of the formula

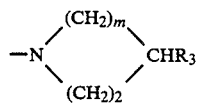

where $R_3$ is H, loweralkyl or aryl, and m is an integer of 1 or 2;

(7) loweralkylene 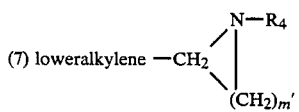

where $R_4$ is H or loweralkyl and m' is an integer of 3 or 4;

(8) -lower alkylene 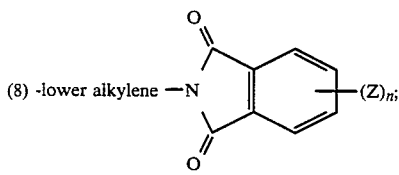

where Z and n are as previously defined;

(9) -loweralkylene 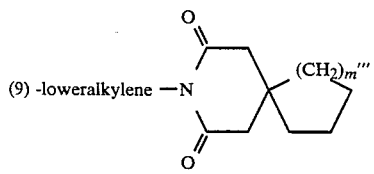

where m''' is an integer of 1,2 or 3;

(10) loweralkynyl 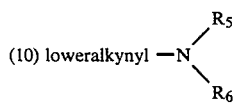

where $R_5$ and $R_6$ are independently alkyl, aryl lower alkyl or are taken together with the N atom to form a substituted or unsubstituted piperidino or pyrrolidino group of the formula

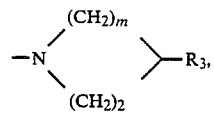

where $R_3$ and m are as defined above;

(11) 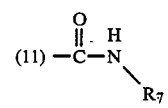

where $R_7$ is loweralkyl, aryl, or aryl lower alkyl;

(12) -loweralkenyl 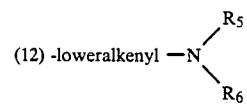

where [$R_1$ and $R_2$]$R_5$ and $R_6$ are as previously defined; and the pharmaceutically acceptable acid addition salts thereof and where applicable to the geometric, stero and optical isomers thereof.

38. The composition as defined in claim 37 wherein R is loweralkyl or arylloweralkyl when $X_1$ and $X_2$ are H.

39. The composition as defined in claim 37 wherein R is loweralkyl or arylloweralkyl when $X_1$ is OH and $X_2$ is H.

40. The composition as defined in claim 37 wherein said compound is isoxazolo[3,4,5-ef][1,4]benzoxazepin-4(5H)-one.

41. The composition as defined in claim 37 wherein said compound is 3-methylisoxazolo[3,4,5-ef][1,4]benzoxazepin-4(5H)-one.

42. The composition as defined in claim 37 wherein said compound is 3,4-dihydro-3-methylisoxazolo[3,4,5-ef][1,4]benzoxazepin-4-ol.

43. The composition as defined in claim 37 wherein said compound is 4,5-dihydroisoxazolo[3,4,5-ef][1,4]benzoxazepin-4-ol.

44. The composition as defined in claim 37 wherein said compound is 3-(3-dimethylaminopropyl)isoxazolo[3,4,5-ef][1,4]benzoxazepin-4(5H)-one.

45. The composition as defined in claim 37 wherein said compound is 3-(3-dimethyl aminopropyl)isoxazolo[3,4,5-ef][1,4]benzoxazepin -4(5H)fumarate.

46. The composition as defined in claim 37 wherein said compound is 4,5-dihydro-3-methylisoxazolo[3,4,5-ef][1,4]benzoxazepine.

47. The composition as defined in claim 37 wherein said compound is 4,5-dihydroisoxazolo[3,4,5-ef][1,4]benzoxazepine.

48. The composition as defined in claim 37 wherein said compound is 4,5-dihydro-3-dimethylaminoethyl)isoxazolo[3,4,5[]1,4]benzoxazepine.

49. The composition as defined in claim 37 wherein said compound is 4,5-dihydro-3-(2-dimethylaminoethyl)isoxazolo[3,4,5-ef][1,4]benzoxazepine.

50. The composition as defined in claim 37 wherein said compound is 4,5-dihydro-3-(4,4-diphenylbutyl)isoxazolo[3,4,5-ef][1,4]benzoxazepine.

51. The composition as defined in claim 37 wherein said compound is isoxazolo[3,4,5-ef][1,4]benzoxazepin-4(5H)-imine.

52. The composition as defined in claim 37 wherein said compound is 3-benzylisoxazolo[3,4,5-ef][1,4]benzoxazepin-4(5H)-one.

53. The composition as defined in claim 37 wherein said compound is 4,5-dihydro-3-(3-dimethylaminopropyl)isoxazolo[3,4,5-ef][1,4]benzoxazepine.

54. The composition as defined in claim 37 wherein said compound is 4,5-dihydro-3-(2-methylaminoethylisoxazolo[3,4,5-ef][1,4]benzoxazepine.

55. The composition as defined in claim 37 wherein said compound is 4,5-dihydro-3-(2-methylaminoethylisoxazolo[3,4,5-ef][1,4]benzoxazepine.

56. The composition as defined in claim 37 wherein said compound is 4,5-dihydro-3-(2-methylaminoethyl)isoxazolo[3,4,5-ef][1,4]benzoxazepine.

57. The composition as defined in claim 37 wherein said compound is 4,5-dihydro-3-(2-propynyl)isoxazolo[3,4,5-ef][1,4]benzoxazepine.

58. The composition as defined in claim 37 wherein said compound is 3-(2-propynyl)isoxazolo[3,4,5-ef][1,4]benzoxazepin-4(5H)-one.

59. The composition as defined in claim 37 wherein said compound is 3-(4-piperidinyl-2-butynyl)isoxazolo[3,4,5-ef][1,4]benzoxazepin-4(5H)-one.

60. The composition as defined in claim 37 wherein said compound is 3-(4-pyrrolidinyl-2-butynyl)isoxazolo[3,4,5-ef][1,4]benzoxazepin-4(5H)-one.

61. The composition as defined in claim 37 wherein said compound is 4,5-dihydro-3-(3-methylaminopropyl)isoxazolo[3,4,5-ef][1,4]benzoxazepine.

62. The composition as defined in claim 37 wherein said compound is 4,5-dihydro-3-(3-methylaminopropyl)isoxazolo[3,4,5-ef][1,4]benzoxazepine hydrochloride, hemihydrate.

63. The composition as defined in claim 37 wherein said compound is 4,5-dihydro-3[(1-methyl-2-pyrrolidinyl)methyl]isoxazolo[3,4,5-ef][1,4]benzoxazepine.

64. The composition as defined in claim 37 wherein said compound is (S)-4,5-dihydro-3-[(1-methyl-2-pyrrolidinyl)methyl]isoxazolo[3,4,5-ef][1,4]benzoxazepine, fumarate, hemi-hydrate.

65. The composition as defined in claim 37 wherein said compound is 4,5-dihydro-3-methylaminocarbonylisoxazolo[3,4,5-ef][1,4]benzoxazepine.

66. The composition as defined in claim 37 wherein said compound is 4,5-dihydro-3-[2-(N-methyl-N-(4-(8-azaspiro[4,5]decan-7,9-dione)butyl)amino) ethyl]isoxazolo-[3,4,5-ef][1,4]benzoxazepine.

67. The composition as defined in claim 37 wherein the compound is 4,5-dihydro-3-[2-(N-methyl-N-(4-(8-azaspiro[4,5]desan-7,9-dione)butyl)amino)ethyl]isoxazolo[3,4,5-ef][1,4]benzoxazepine sesquifumarate.

68. The composition as defined in claim 37 wherein said compound is 4,5-dihydro-3-[3-(N-methyl-N-(4-(8-azaspiro[4,5]decan-7,9-dione) butyl)amino)propyl]isoxazolo[3,4,5-ef][1,4]benzoxazepine.

69. The composition as defined in claim 37 wherein said compound is 4,5-dihydro-3-[3-(N-methyl-N-(4-(8-azaspiri[4,5]decan-7,9-dione)butyl) amino)propyl]isoxazolo[3,4,5-ef][1,4]benzoxazepine, hydrochloride, hemihydrate.

70. The composition as defined in claim 37 wherein said compound is 3-(2-phthalimidoethyl)isoxazolo[3,4,5-ef][1,4]benzoxazepin-4(5H)-one.

71. The composition as defined in claim 37 wherein said compound is 8-[4-(4,5-dihydro-4-oxoisoxazolo[3,4,5-ef][1,4]benzoxazepin-3-yl)butyl]-8-azaspiro[4,5]decan-7,9-dione.

72. The composition as defined in claim 37 wherein said compound is 3-[4-(4-phenylpiperidinyl)-2-butynyl]-isoxazolo[3,4,5-ef][1,4]benzoxazepin-4(5H)-one.

73. A method of alleviating pain in a mammal in need thereof which comprises administering an effective pain-alleviating amount of a compound having the formula

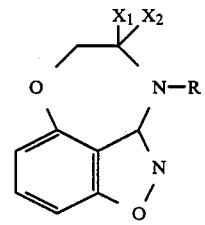

wherein $X_1$ is H; $X_2$ is H or OH; or $X_1$ and $X_2$ taken together are carbonyl oxygen or

R is (1) H, (2) loweralkyl, (3) arylloweralkyl, (4) loweralkynyl, (5) loweralkenyl,

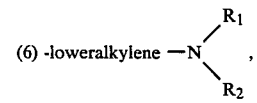

where $R_1$ and $R_2$ are independently (a) H, (b) lower alkyl, (c) arylloweralkyl,

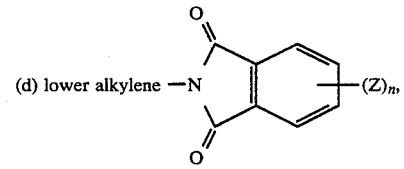

where Z is H, halogen, loweralkyl, loweralkoxy, $CF_3$, nitro or amino and n is an integer of 1 to 3;

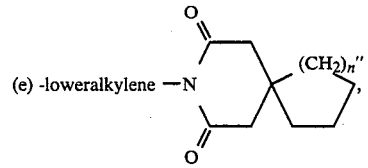

where n" is an integer of 1 to 3; or (f) $R_1$ and $R_2$ taken together with the nitrogen atom are substituted or unsubstituted piperidino or pyrrolidino of the formula

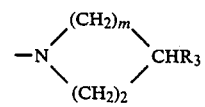

where $R_3$ is H, loweralkyl or aryl, and m is an integer of 1 or 2;

(7) loweralkylene 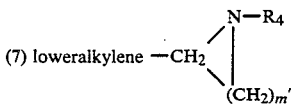

where R₄ is H or loweralkyl and m' is an integer of 3 or 4;

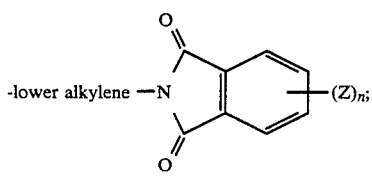

where Z and n are as previously defined;

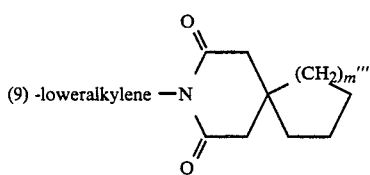

where m''' is an integer of 1,2 or 3;

(10) loweralkynyl 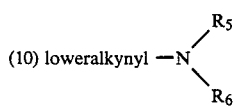

where $R_5$ and $R_6$ are independently alkyl, aryl lower alkyl or are taken together with the N atom to form a substituted or unsubstituted piperidino or pyrrolidino group of the formula

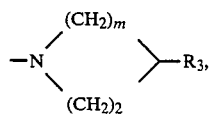

where $R_3$ and m are as defined above;

(11) 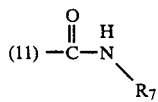

where $R_7$ is loweralkyl, aryl, or aryl lower alkyl;

(12) -loweralkenyl 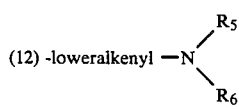

where [$R_1$ and $R_2$]$R_5$ and $R_6$ are as previously defined; and the pharmaceutically acceptable acid addition salts thereof and where applicable to the geometric and stero isomers thereof.

74. The method as defined in claim 73 wherein R is loweralkyl or arylloweralkyl when $X_1$ and $X_2$ are H.

75. The method as defined in claim 73 wherein said R is loweralkyl or arylloweralkyl when $X_1$ is OH and $X_2$ is H.

76. The method as defined in claim 73 wherein said compound is isoxazolo[3,4,5-ef][1,4]benzoxazepin-4(5H)-one.

77. The method as defined in claim 73 wherein said compound is 3-methylisoxazolo[3,4,5-ef][1,4]benzoxazepin-4(5H)-one.

78. The method as defined in claim 73 wherein said compound is 4,5-dihydro-3-methylisoxazolo[3,4,5-ef][1,4]benzoxazepin-4-ol.

79. The method as defined in claim 73 wherein said compound is 4,5-dihydroisoxazolo[3,4,5-ef][1,4]benzoxazepin-4-ol.

80. The method as defined in claim 73 wherein said compound is 3-(3-dimethylaminopropyl)isoxazolo[3,4,5-ef][1,4]benzoxazepin-4(5H)-one.

81. The method as defined in claim 73 wherein said compound comprises the fumarate salt.

82. The method as defined in claim 73 wherein said compound is 4,5-dihydro-3-methylisoxazolo[3,4,5-ef][1,4]benzoxazepine.

83. The method as defined in claim 73 wherein said compound is 4,5-dihydroisoxazolo[3,4,5-ef][1,4]benzoxazepine.

84. The method as defined in claim 73 wherein said compound is 4,5-dihydro-3-(2-dimethylaminoethyl)isoxazolo[3,4,5-ef][1,4]benzoxazepine.

85. The method as defined in claim 84 wherein said compound comprises the sesquifumarate salt.

86. The method as defined in claim 73 wherein said compound is 4,5-dihydro-3-(4,4-diphenylbutyl)isoxazolo[3,4,5-ef][1,4]benzoxazepine.

87. The method as defined in claim 73 wherein said compound is isoxazolo[3,4,5-ef][1,4]benzoxazepin-4(5H)-imine.

88. The method as defined in claim 73 wherein said compound is 3-benzylisoxazolo[3,4,5-ef][1,4]benzoxazepin-4(5H)-one.

89. The method as defined in claim 73 wherein said compound is 4,5-dihydro-3-(3-dimethylaminopropyl)isoxazolo[3,4,5-ef][1,4]benzoxazepine.

90. The method as defined in claim 89 wherein said compound comprises the sesquifumarate salt.

91. The method as defined in claim 73 wherein said compound is 4,5-dihydro-3-(2-methylaminoethyl)isoxazolo[3,4,5-ef][1,4]benzoxazepine.

92. The method as defined in claim 91 wherein said compound comprises the hydrochloride salt.

93. The method as defined in claim 73 wherein said compound is 4,5-dihydro-3-(2-propynyl)isoxazolo[3,4,5-ef][1,4]benzoxazepine.

94. The method as defined in claim 73 wherein said compound is 3-(2-propynyl)isoxazolo[3,4,5-ef][1,4]benzoxazepin-4(5H)-one.

95. The method as defined in claim 73 wherein said compound is 3-(4-piperidinyl-2-butynyl)isoxazolo[3,4,5-ef][1,4]benzoxazepin-4(5H)-one.

96. The method as defined in claim 73 wherein said compound is 3-(4-pyrrolidinyl-2-butynyl)isoxazolo[3,4,5-ef][1,4]benzoxazepin-4(5H)-one.

97. The method as defined in claim 73 wherein said compound is 4,5-dihydro-3-(3-methylaminopropyl)isoxazolo[3,4,5-ef][1,4]benzoxazepine.

98. The method as defined in claim 73 wherein said compound is 4,5-dihydro-3-(3-methylaminopropyl)isoxazolo[3,4,5-ef][1,4]benzoxazepine hydrochloride, hemihydrate.

99. The method as defined in claim 73 wherein said compound is 4,5-dihydro-3[(1-methyl-2-pyrrolidinyl)methyl]isoxazolo[3,4,5-ef][1,4]benzoxazepine.

100. The method as defined in claim 73 wherein said compound is (S)-4,5-dihydro-3-[(1-methyl-2-pyrrolidinyl)methyl]isoxazolo[3,4,5-ef][1,4]benzoxazepine, fumarate, hemi-hydrate.

101. The method as defined in claim 73 wherein said compound is 4,5-dihydro-3-methylaminocarbonylisoxazolo[3,4,5-ef][1,4]benzoxazepine.

102. The method as defined in claim 73 wherein said compound is 4,5-dihydro-3-[2-(N-methyl-N-(4-(8-azaspiro[4,5]decan-7,9-dione) butyl)amino)ethyl]isoxazolo-[3,4,5-ef][1,4]benzoxazepine.

103. The method as defined in claim 102 wherein said compound comprises the sesquifumarate salt.

104. The method as defined in claim 73 wherein said compound is 4,5-dihydro-3-[3-(N-methyl-N-(4-(8-azaspiro[4,5]decan-7,9-dione) butyl)amino)propyl]-isoxazolo[3,4,5-ef][1,4]benzoxazepine.

105. The method as defined in claim 73 wherein said compound is 4,5-dihydro-3-[3-(N-methyl-N-(4-(8-azaspiri[4,5]decan-7,9-dione) butyl)amino)propyl]isoxazolo[3,4,5-ef][1,4]benzoxazepine, hydrochloride, hemihydrate.

106. The method as defined in claim 73 wherein said compound is 3-(2-phthalimidoethyl)isoxazolo[3,4,5-ef][1,4]benzoxazepin-4(5H)-one.

107. The method as defined in claim 73 wherein said compound is 8-[4,5-dihydro-4-oxoisoxazolo[3,4,5-ef][1,4]benzoxazepin-3-yl)butyl]-8-azaspiro[4,5]decan-7,9-dione.

108. The method as defined in claim 73 wherein said compound is 3-[4-(4-phenylpiperidinyl)-2-butynyl]-isoxazolo[3,4,5-ef][1,4]benzoxazepin-4(5H)-one.

* * * * *